United States Patent
Burt

(10) Patent No.: US 11,116,522 B2
(45) Date of Patent: Sep. 14, 2021

(54) ARTHROSCOPIC TOTAL SHOULDER ARTHROPLASTY

(71) Applicant: David Michael Burt, Plainfield, IL (US)

(72) Inventor: David Michael Burt, Plainfield, IL (US)

( * ) Notice: Subject to any disclaimer, the term of this patent is extended or adjusted under 35 U.S.C. 154(b) by 132 days.

(21) Appl. No.: 16/021,263

(22) Filed: Jun. 28, 2018

(65) Prior Publication Data

US 2018/0368859 A1 Dec. 27, 2018

Related U.S. Application Data

(63) Continuation of application No. 13/293,767, filed on Nov. 10, 2011, now Pat. No. 10,039,556.

(51) Int. Cl.
| | |
|---|---|
| *A61B 17/17* | (2006.01) |
| *A61F 2/40* | (2006.01) |
| *A61B 17/16* | (2006.01) |
| *A61F 2/30* | (2006.01) |
| *A61F 2/46* | (2006.01) |
| *A61B 17/86* | (2006.01) |

(52) U.S. Cl.
CPC ...... *A61B 17/1684* (2013.01); *A61B 17/1778* (2016.11); *A61F 2/4003* (2013.01); *A61B 17/86* (2013.01); *A61F 2002/30179* (2013.01); *A61F 2002/30332* (2013.01); *A61F 2002/30471* (2013.01); *A61F 2002/30579* (2013.01); *A61F 2002/30904* (2013.01); *A61F 2002/4007* (2013.01); *A61F 2002/4635* (2013.01)

(58) Field of Classification Search
CPC . A61B 17/1778; A61B 17/1684; A61B 17/86; A61F 2002/4687; A61F 2/4003; A61F 2002/30179; A61F 2002/30332; A61F 2002/30471; A61F 2002/30579; A61F 2002/30904; A61F 2002/4007; A61F 2002/4635
See application file for complete search history.

(56) References Cited

U.S. PATENT DOCUMENTS

| 2,685,877 A | 8/1954 | Dobelle |
| 4,550,450 A | 11/1985 | Kinnett |
(Continued)

FOREIGN PATENT DOCUMENTS

WO WO/2009/152270 12/2009

OTHER PUBLICATIONS

Kasper, James C., Itamura, John M., Tibone, James E., Levin, Scott L., Stevanovic, Milan V., Human cadaveric study of subscapularis muscle innervation and guidelines to prevent denervation, J Shoulder Elbow Surg. Jul./Aug. 2008, vol. 17, No. 4, pp. 659-662.

(Continued)

*Primary Examiner* — Bruce E Snow
*Assistant Examiner* — Melissa A Hoban
(74) *Attorney, Agent, or Firm* — McDonald Hopkins LLC

(57) ABSTRACT

The current invention appropriately places stable implants into both sides of the shoulder joint to relieve pain and restore function in an arthritic shoulder, and does so in a manner that is arthroscopic, that does not violate the muscles about the shoulder or other vital structures, and that allows for immediate active or voluntary movement by the patient after surgery.

13 Claims, 22 Drawing Sheets

(56) References Cited

U.S. PATENT DOCUMENTS

| | | | |
|---|---|---|---|
| 5,163,961 | A | 11/1992 | Harwin |
| 5,409,494 | A | 4/1995 | Morgan |
| 5,741,335 | A | 4/1998 | Gerber |
| 6,013,083 | A | 1/2000 | Bennett |
| 6,589,281 | B2 | 7/2003 | Hyde |
| 6,613,093 | B2 | 9/2003 | DeCarlo |
| 6,699,289 | B2 | 3/2004 | Iannotti |
| 7,901,408 | B2 | 3/2011 | Ek |
| 2002/0133153 | A1 | 9/2002 | Hyde |
| 2003/0125810 | A1 | 7/2003 | Sullivan |
| 2004/0010257 | A1 | 1/2004 | Cachia |
| 2004/0167629 | A1 | 8/2004 | Geremakis |
| 2005/0049712 | A1 | 3/2005 | Ondrla |
| 2005/0216008 | A1 | 9/2005 | Zwimmann |
| 2006/0074421 | A1 | 4/2006 | Bickley |
| 2006/0142871 | A1 | 6/2006 | Biss |
| 2006/0276897 | A1 | 12/2006 | Winslow |
| 2007/0050040 | A1 | 3/2007 | Guederian |
| 2008/0132896 | A1 | 6/2008 | Bowen |
| 2008/0177272 | A1 | 7/2008 | Zucherman |
| 2009/0018542 | A1 | 1/2009 | Saravia |
| 2009/0254093 | A1* | 10/2009 | White .............. A61B 17/175 606/89 |
| 2010/0049260 | A1 | 2/2010 | Long |
| 2010/0057210 | A1 | 3/2010 | Ondrla |
| 2010/0069913 | A1 | 3/2010 | Chirico |
| 2010/0087877 | A1 | 4/2010 | Gunther |
| 2010/0121337 | A1 | 5/2010 | Pandya |
| 2010/0324607 | A1 | 12/2010 | Davis |
| 2011/0046682 | A1 | 2/2011 | Stephan |
| 2011/0082551 | A1 | 4/2011 | Kraus |
| 2011/0087227 | A1 | 4/2011 | Mazur |
| 2011/0106086 | A1 | 5/2011 | Laird |
| 2011/0106177 | A1 | 5/2011 | Lewis |
| 2011/0184419 | A1* | 7/2011 | Meridew .......... A61B 17/1746 606/80 |
| 2012/0016485 | A1 | 1/2012 | Sharp |
| 2012/0046752 | A1 | 2/2012 | Blanchard |
| 2012/0109137 | A1* | 5/2012 | Iannotti .......... A61B 17/1746 606/87 |
| 2012/0116530 | A1 | 5/2012 | Forsell |

OTHER PUBLICATIONS

Miller, Bruce S., Joseph, Thomas A., Noonan, Thomas J., Horan, Marilee P., Hawkins, Richard J., Rupture of the subscapularis tendon after shoulder arthroplasty: Diagnosis, treatment, and outcome, J Shoulder Elbow Surg., Sep./Oct. 2005, vol. 14, No. 5, pp. 492-496.

Lynch, Nancy M., Cofield, Robert H., Silbert, Peter L., Hermann, Robert C., Neurologic complications after total shoulder arthroplasty, J. Shoulder Elbow Surg., Jan./Feb. 1996, vol. 5, No. 1, pp. 53-61.

Miller, Suzanne L., Hazrati, Yassamin, KLEPPS, Steven, FLATOW, Evan L., Loss of subscapularis function after total shoulder replacement: A seldom recognized problem, J Shoulder Elbow Surg., Jan./Feb. 2003, vol. 1, No. 1, pp. 29-34.

Williams, Gerald R., Jr., WONG, Kirk L., Pepe, Matthew D., Tan, Virak, Silverberg, David, Ramsey, Matthew L., Karduna, Andrew, Iannotti, Joseph P., The effect of articular malposition after total shoulder arthroplasty on glenohumeral translations, range of motion, and subacromial impingement, J Shoulder Elbow Surg., Sep./Oct. 2001, vol. 10, No. 5, pp. 399-409.

Strauss, Eric J., Roche, Chris, Flurin, Pierre-Henri, Wright, Thomas, Zuckerman, Joseph D., The glenoid in shoulder arthroplasty, Journal of Shoulder and Elbow Surgery Board of Trustees, (2009) 18, pp. 819-833.

Qureshi, Sheeraz, Hsiao, Andrew, Klug, Raymond A., Lee, Ed, Braman, Jonathan, Flatow, Evan L., Subscapularis function after total shoulder replacement: Results with lesser tuberosity osteotomy, J Shoulder Elbow Surg., vol. 17, No. 1, Jan./Feb. 2008, pp. 68-72.

Lafosse, Laurent, Schnaser, Erik, Haag, Manuel, Gobezie, Reuben, Primary total shoulder arthroplasty performed entirely thru the rotator interval: Technique and minimum two-year outcomes, J Shouler Elbow Surg (2009), 18, pp. 864-873.

Boileau, Pascal, Avidor, Cyril, Krishnan, Sumant G., Walch, Gilles, Kempf, Jean-Francois, Mole, Daniel, Cemented polyethylene versus uncemented metal-backed glenoid components in total shoulder arthroplasty: A prospective. double-blind. randomized study. J Shoulder Elbow Surg., Jul./Aug. 2002, vol. 11, No. 4, pp. 351-359.

* cited by examiner

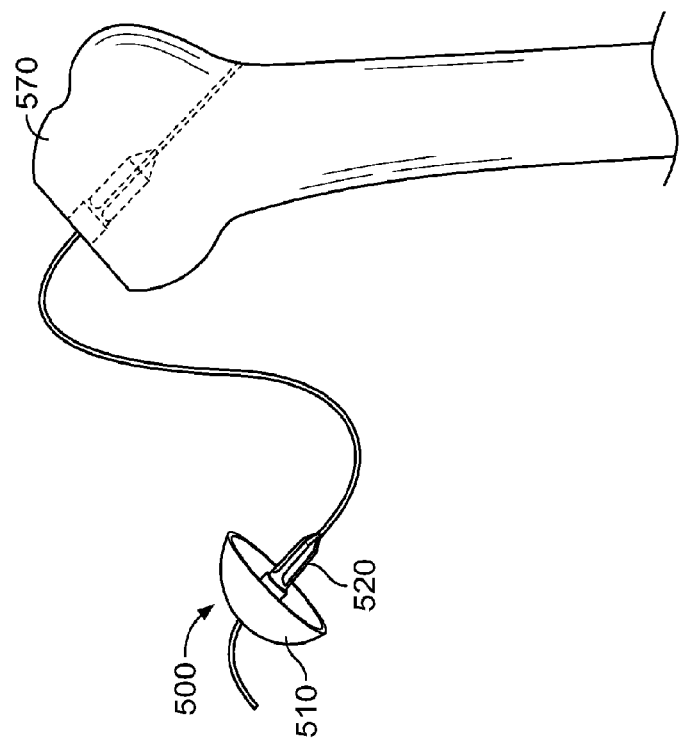
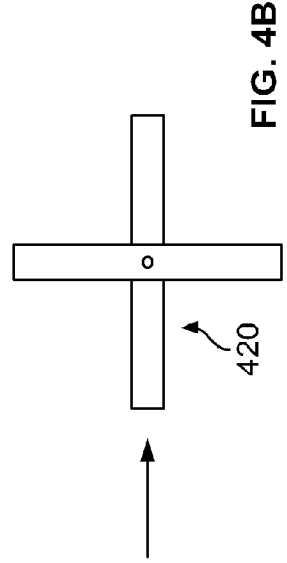
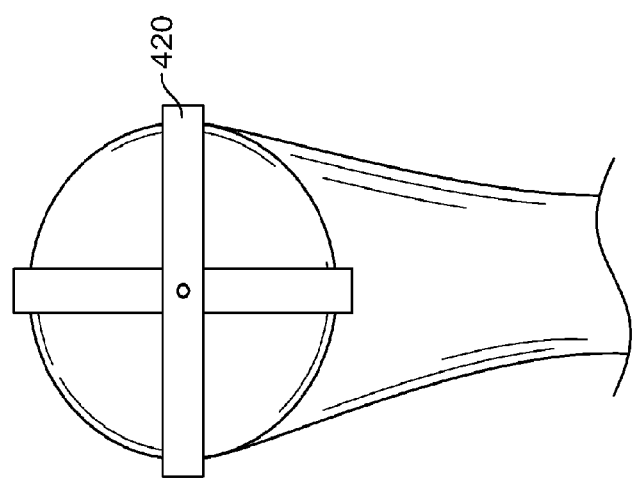
FIG. 4A
FIG. 4B
FIG. 5

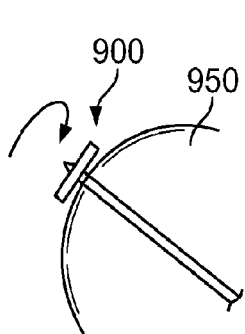 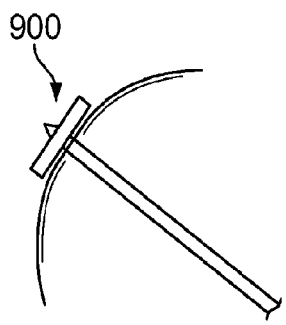 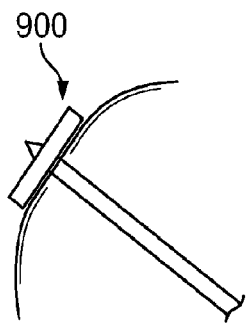
FIG. 9C    FIG. 9D    FIG. 9E
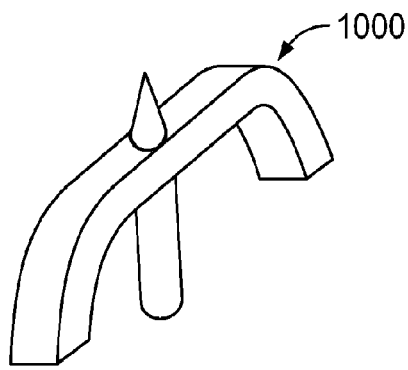
FIG. 10A
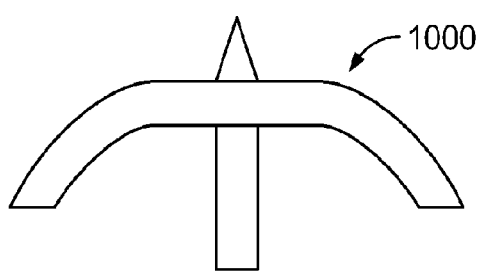
FIG. 10B
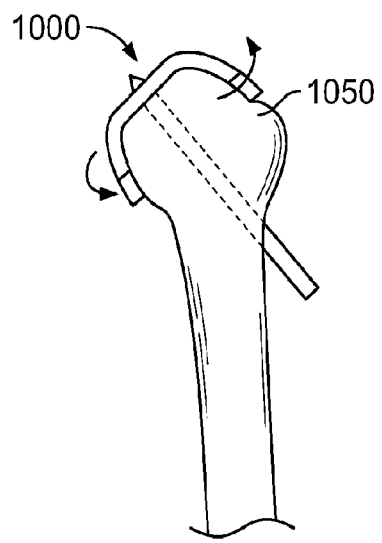
FIG. 10C

ARTHROSCOPIC TOTAL SHOULDER ARTHROPLASTY

CROSS-REFERENCE TO RELATED APPLICATION

This application is a continuation of U.S. patent application Ser. No. 13/293,767, filed Nov. 10, 2011, and entitled "ARTHROSCOPIC TOTAL SHOULDER ARTHROPLASTY," the entirety of which is incorporated herein by reference.

This application relates to methods, instrumentation, and implants for orthopedic surgery and more particularly to devices for arthroscopic total shoulder arthroplasty.

BACKGROUND

Orthopedic surgeons perform joint replacement surgery for patients who suffer pain and physical limitations caused by joint surfaces that have been damaged by degenerative, traumatic, or other pathologic processes. The functional outcome from these joint replacement surgeries is directly related to the degree of morbidity associated with the surgical method and the ability of the method to best restore the natural anatomy and biomechanics of the joint. Orthopedic surgeons are continually searching for ways to improve outcomes for joint replacement surgery by developing methods of less invasive surgery to limit surgical morbidity and by developing novel methods and implants to better restore the native joint anatomy.

Conventional shoulder replacement surgery has several limitations. It requires an extensive exposure that irreversibly damages the rotator cuff and still fails to gain sufficient joint access to properly restore the native anatomic relationships of both the humeral head and glenoid surfaces. Also, there remain issues with glenoid implant fixation and early loosening.

Surgical replacement of the shoulder joint requires large incisions and dislocation of the shoulder which can be detrimental to the function of the shoulder postoperatively.

One of the major technical challenges to traditional open incision shoulder arthroplasty is the requirement of surgical release of the subscapularis muscle at the front of the shoulder. Conventional methods utilize a large anterior deltopectoral exposure. The anterior humeral circumflex blood vessels are typically ligated and the anterior (subscapularis) musculotendinous unit is transected. The shoulder must then be completely dislocated both anteriorly and posteriorly to prepare the humeral and glenoid joint surfaces. This can cause excessive traction on the arm which has resulted in injury to the nerves of the brachial plexus.

The amount of time spent waiting for this muscle to heal post-operatively, typically 6 weeks, can be detrimental to the overall outcome in the long term. The literature has also demonstrated that even with perfect technical handling of this muscle that the muscle function itself is altered such that it may never return to normal. Lynch N. M., et al., *Neurologic Complications After Total Shoulder Arthroplasty*, J. Shoulder Elbow Surg., 1996; 5(1) at 53-61; James C. Kasper, et al., Journal of Shoulder and Elbow Surgery, July, 2008 Vol. 17, Issue 4, at 659-662; Kamal I. Bohsali, et al. *Complications of Total Shoulder Arthroplasty*, J. Bone Joint Surg. Am., October 2006; 88 at 2279-2292.

Additionally, if this muscle fails to heal properly, either due to biologic failure or technical failure of repair, then complications can ensue which may include instability or dislocation of the shoulder, weakness, loosening of implants, loss of function, and need for revision surgery. Bruce S. Miller, et al. Journal of Shoulder and Elbow Surgery, September 2005 Vol. 14, Issue 5, at 492-496.

With regards to shoulder replacement surgery, all conventional methods require surgical transection of a rotator cuff tendon to gain sufficient exposure of the joint surfaces of the shoulder. See U.S. Pat. No. 4,550,450, entitled, "Total Shoulder Prosthesis System," which is incorporated herein by reference. After the joint surfaces are replaced, the rotator cuff tendon must be surgically repaired with suture material. This tenuous repair necessitates an obligatory period of approximately six weeks for the rotator cuff tendon to heal before advanced shoulder rehabilitation can be performed. This surgical transection and subsequent repair, as well as the delay in rehabilitation, hold significant consequences for the functional outcome of the shoulder replacement including permanent weakness and decreased range of motion. Miller S. L. et al., *Loss of Subscapularis Function After Total Shoulder Replacement: A Seldom Recognized Problem*, J. Shoulder Elbow Surg., January-February 2003, 12(1), at 29-34.

Additionally, despite the extensive exposure, conventional methods for shoulder replacement surgery still fail to properly restore the native anatomic relationships of the joint surfaces of the shoulder. Conventional methods prepare the humeral surfaces of the shoulder joint by referencing off the intramedullary axis of the humeral shaft. This poses great difficulty for the surgeon since the intramedullary axis has an inconsistent relationship to the humeral surface. The humeral joint surface also possesses a complex anatomy with significant variability which cannot be entirely restored with conventional methods and implants. There exists much variability in the humeral head neck-shaft angle, posterior and medial offset, version (rotation), height, thickness, and radius of curvature. Boileau P., et al., *The Three-Dimensional Geometry of the Proximal Humerus*, J. Bone Joint Surg. Br., 1997, 79B, at 857-865; Iannotti J. P., et al., *The Normal Glenohumeral Relationships. An Anatomic Study of One Hundred and Forty Shoulders*, J. Bone Joint Surg., 1992; 74A(4), at 491-500; McPherson E. J., et al., *Anthropometric Study of Normal Glenohumeral Relationships*, J. Shoulder Elbow Surg., 1997; 6, at 105-112; Soslowsky L. J., et al., *Articular Geometry of the Glenohumeral Joint*, Clin. Orthop., 1992, 285, at 181-190. The failure to restore the native anatomic relationships and biomechanics to the shoulder joint has proven to result in a significantly lesser functional and durable outcome. Williams G. R., et al., *The Effect of Articular Malposition and Shoulder Arthroplasty on Glenohumeral Translations, Range of Motion, and Subacromial Impingement*, J. Shoulder Elbow Surg., 2001; 10(5), at 399-409.

Shoulder arthritis is a debilitating problem that is treated by many orthopedic surgeons. The goals of surgery are restoration of shoulder function and decreased pain via the replacement of damaged arthritic joint surfaces with prosthetic devices that will be durable in the long term. Surfaces that are replaced include the humerus ("ball") and the glenoid ("socket") which is a part of the scapula bone. Michael A. Wirth, et al., J. Bone Joint Surg. Am., May, 2006, 88, at 964-973.

The primary objective of an arthroscopic approach is to spare the subscapularis muscle and the other rotator cuff muscle such that immediate and active movement of the shoulder can be achieved directly after surgery without delay to wait for healing. Additionally the risk of muscle dysfunction due to its violation at the time of surgery is avoided, and the complication subscapularis muscle detachment and the ensuing instability will be avoided, and thus patient satisfaction improved. Laurent Lafosse, et al., *Primary Total Shoulder Arthroplasty Performed Entirely Thru the Rotator Interval: Technique and Minimum Two-Year Outcomes*, Jun. 22, 2009, Journal of Shoulder and Elbow Surgery, November, 2009 Vol. 18, Issue 6, at 864-873.

Another current problem with shoulder replacement is that the primary cause for revision shoulder replacement surgery in long term outcome studies remains loosening of the glenoid component. Eric J. Strauss, et al., Journal of Shoulder and Elbow Surgery, September, 2009, Vol. 18, Issue 5, at 819-833. The majority of these implants have been made of high-density polyethylene, which are cemented into bone. Many have also been older generation metal-backed components which were also cemented into bone.

Additionally, the thickness of the implants causes the articulation of prosthetic implants to occur further away or laterally from the natural and native anatomy of the shoulder joint. This has been implicated in a method of loosening the glenoid component that has been referred to as the "rocking horse" effect. The lateralized position of the glenoid component allows for load to occur unevenly upon the joint and the glenoid component rocking it back and forth and causing it to separate from the bone and loosen.

As to the problem of rotator cuff (subscapularis muscle) dysfunction, rupture, or failure of repair postoperatively, modifications have been attempted to improve results which include removing the muscle with attached bone and repair of said construct at the time of surgery. Sheeraz Qureshi, et al., *Subscapularis Function After Total Shoulder Replacement: Results With Lesser Tuberosity Osteotomy*, Nov. 16, 2007, Journal of Shoulder and Elbow Surgery, January, 2008, Vol. 17, Issue 1, at 68-72. Other investigators have used either a subscapularis and rotator cuff sparing open approach to the shoulder or a partial release of the subscapularis with good short term results. Laurent Lafosse, et al., *Primary Total Shoulder Arthroplasty Performed Entirely Thru the Rotator Interval: Technique and Minimum Two-Year Outcomes*, Jun. 22, 2009, Journal of Shoulder and Elbow Surgery, November, 2009 Vol. 18, Issue 6, at 864-873; Felix A. Savoie, MD, Unpublished Internet Communication, www.vumedi.com, 2010. These are open procedures that have also been described as arthroscopically assisted for capsular release or removal of osteophytes (bone spurs).

Regarding loosening of the glenoid component, newer generation designs for open surgery show promise in early results but no long term data exists yet to show superiority over older designs. These include metal backed or hybrid components that allow bone to engage and "grow into" the component for theoretical permanent union between the two and stability. Pascal Boileau, et al., *Cemented Polyethylene Versus Uncemented Metal-Backed Glenoid Components in Total Shoulder Arthroplasty A Prospective, Double-Blind, Randomized Study*, Journal of Shoulder and Elbow Surgery, July, 2002, Vol. 11, Issue 4, at 351-359.

Arthroscopic options have been described in the literature which to date have been proposed as short to medium term alternatives for younger patients and potentially as a stepping stone prior to traditional open shoulder arthroplasty. Long terms outcomes at best have been described as 5-7 years. Weber et al., Arthroscopy; deBeer et al., Arthroscopy, May, 2006, Vol. 22, No. 5, at 570. el-570. el5; Burkhart, et al., Arthroscopy, September, 2007, Vol. 23, No. 9 at 1019-1022; Savoie et al., Arthroscopy, August, 2009, Vol. 25, No. 8, at 864-871. These techniques include removal of osteophytes, reshaping of humeral and glenoid bone, release of tight capsular structures, and in some cases interposition of various allograft biologic or synthetic allograft material between the glenoid and humerus to act as a cushion for the joint.

SUMMARY OF INVENTION

The present invention relates to a humeral implant comprising an in-growth stem having a plurality of movable flanges and a humeral surface bearing portion. The humeral implant may comprise a hemispherical implant, an implant backing and a stem. The humeral implant may be short-stemmed and comprise a base plate and a stem having a folding mechanism where the stem extends from the base plate.

The present invention also relates to a glenoid implant comprising a stemmed or pegged inset device that has a base plate, a central peg or central stem located near the center of the base plate, and flanges extending from the central peg or central stem.

The present invention further relates to an implant assembly having a humeral implant comprising at least one of a humeral surface bearing portion, a hemispherical implant and implant backing, and a base plate, and a stem having a plurality of movable flanges. The implant assembly may also include a glenoid implant comprising a base plate, a central peg or central stem located near the center of the base plate; and flanges extending from the central peg or central stem.

BRIEF DESCRIPTION OF THE DRAWINGS

Embodiments of the present disclosure are described herein with reference to the drawings wherein:

FIG. 4A is a perspective view of an embodiment of a multi humeral resurfacing implant;

FIG. 4B is a schematic view of an embodiment of a hemispherical implant;

FIG. 5 is a perspective view of an embodiment of a stemmed base plate;

FIG. 9C is a side view of an embodiment of a flat reamer circular spinning in a humerus;

FIG. 9D is a side view of an embodiment of a flat reamer after circular spinning in a humerus;

FIG. 9E is a zoomed in side view of an embodiment of a flat reamer after circular spinning in a humerus;

FIG. 10A is a perspective view of an embodiment of a rounded, low profile reamer;

FIG. 10B is a schematic view of an embodiment of a rounded, low profile reamer;

FIG. 10C is a side view of an embodiment of a rounded, low profile reamer circular spinning in a humerus;

FIG. 24B-2 is a schematic and side view of an embodiment of an unfolded template engaging a bone;

FIG. 24C-1 is a schematic and side view of an embodiment of a folded opened t-shape template engaging a bone;

FIG. 24C-2 is a schematic and side view of an embodiment of an unfolded opened t-shape template engaging a bone.

DETAILED DESCRIPTION OF THE PREFERRED EMBODIMENTS

The following is related to methods, instrumentation, and implants for orthopedic surgery and more particularly to devices for arthroscopic total shoulder arthroplasty.

The current invention appropriately places stable implants into both sides of the shoulder joint to relieve pain and restore function in an arthritic shoulder, and does so in a manner that is arthroscopic, that does not violate the muscles about the shoulder or other vital structures, and that allows for immediate active or voluntary movement by the patient after surgery.

Another advantage of the current invention is that it allows for access to the shoulder (gleno-humeral) joint without large incisions and without violation of the subscapularis muscle or any of the rotator cuff muscles through an arthroscopic approach via small incisions (such as about 1-2 cm, about 0.5-2.5 cm, about 0.2-2.7 cm, and about 0.1-1.5 cm), and the placement of definitive prosthetic implants for both ball and socket sides of the joint through the same.

An implant assembly is generally provided. The components of the implant assembly may be made of any appropriate material such as metal, tantalum, porous metal, trabecular metal, cobalt chrome, ceramic materials, magnetic metals, titanium, steel, plastic, polymers, polyethylene, bony in-growth material, other suitable materials, and combinations of two or more materials thereof.

The implant assembly includes at least one of a humeral implant, a glenoid implant, implantation surgical devices, or a combination of two or more thereof.

The humeral implant may be a humeral resurfacing implant or a short-stemmed humeral implant. The humeral implant may be made of any appropriate material such as metal, tantalum, porous metal, trabecular metal, cobalt chrome, ceramic materials, magnetic metals, titanium, steel, plastic, polymers, polyethylene, bony in-growth material, other suitable materials, and combinations of two or more materials thereof.

In an embodiment, the humeral resurfacing implant is a multi humeral resurfacing implant. The multi humeral resurfacing implant comprises at least two components. The multi humeral resurfacing implant may be made of any appropriate material such as metal, tantalum, porous metal, trabecular metal, cobalt chrome, ceramic materials, magnetic metals, titanium, steel, plastic, polymers, polyethylene, bony in-growth material, other suitable materials, and combinations of two or more materials thereof.

Figure 1B:
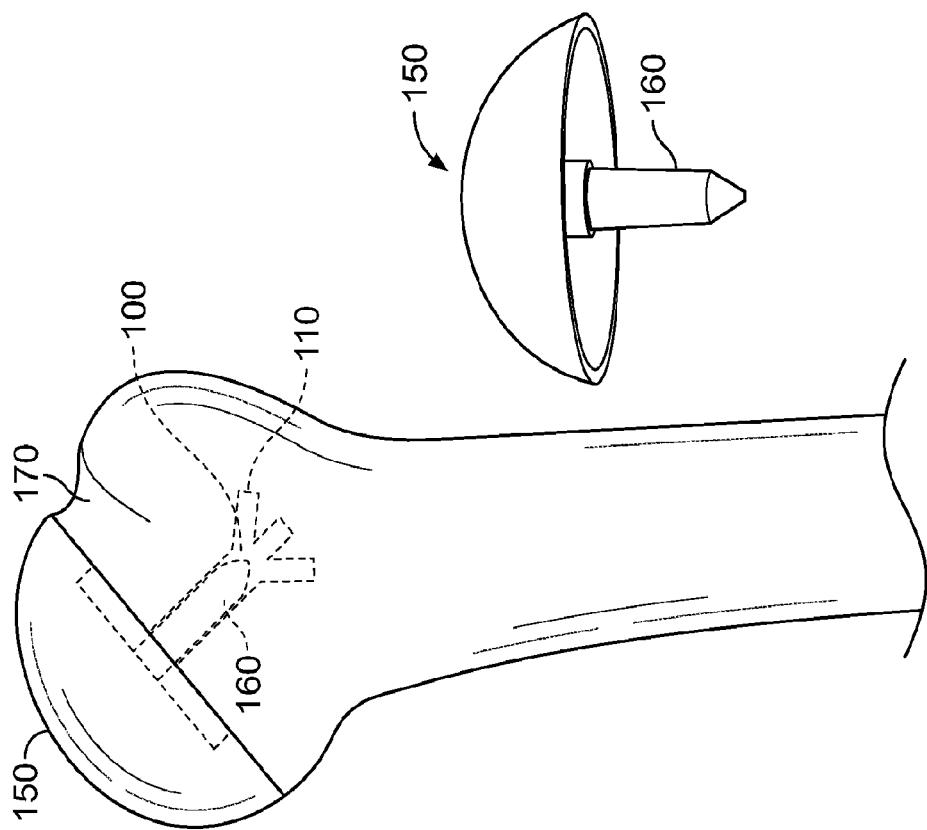
FIG. 1B is a schematic view of an embodiment of an in-growth stem inserted into a humerus.
Figure 1A:
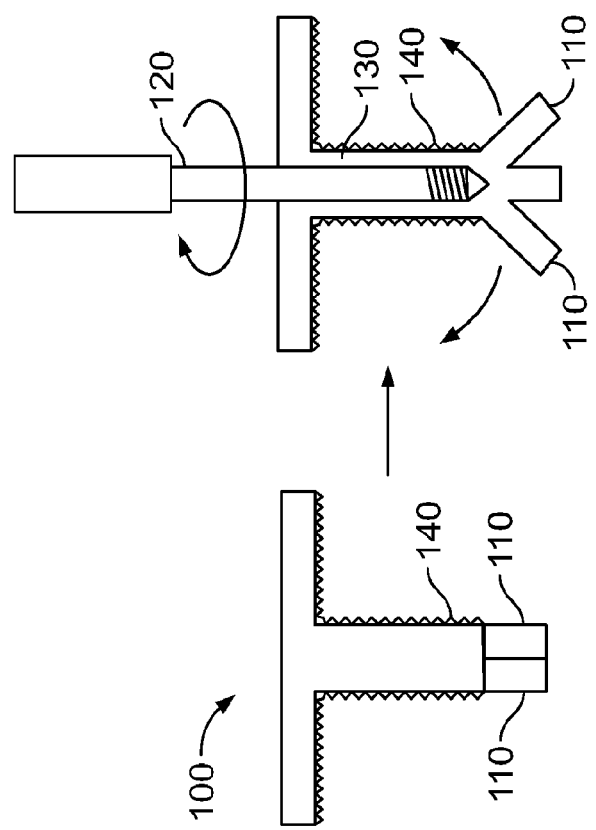
FIG. 1A is a schematic view of an embodiment of an in-growth stem with flanges going from folded to unfolded.

The multi humeral resurfacing implant comprises an in-growth stem 100 and a humeral surface bearing portion 150, as shown in FIGS. 1A and 1B. For example, the in-growth stem may be, but is not limited to, a bony in-growth stem, a Trabecular Metal™ in-growth stem, or other in-growth stems. As shown in FIG. 1B, the in-growth stem 100 may be inserted into a native humerus bone 170.

The in-growth stem 100 may engage the humeral surface bearing portion 150 to form a humeral resurfacing implant. As shown in FIGS. 1A and 1B, the in-growth stem 100 contains a female receptive opening 130 for engaging a male counterpart 160 of the humeral surface bearing portion 150. In an alternative embodiment, the in-growth stem 100 contains a male tower for engaging the humeral surface bearing portion that contains a female receptive end. The in-growth stem 100 may engage the humeral surface bearing portion 150 in a taper-lock fashion or other engaging fashions.

The in-growth stem 100 may include an unfolding series of flanges 110 at the tip of the stem that may deploy to further engage and lock into the native bone of the humerus 170, as shown in FIGS. 1A and 1B. The metal flanges 110 may engage and lock into the native bone of the humerus 170 by any engaging means such as, but not limited to, a screw/screwdriver mechanism 120. The engaging means may be employed either in an antegrade or retrograde (trans-humeral) fashion to further stabilize the bony in-growth stem 100.

The in-growth stem 100 may further comprise serrated edges 140 on its exterior to further engage the native bone of the humerus 170 and lock the in-growth stem 100 into the native bone of the humerus 170.

Figure 2:
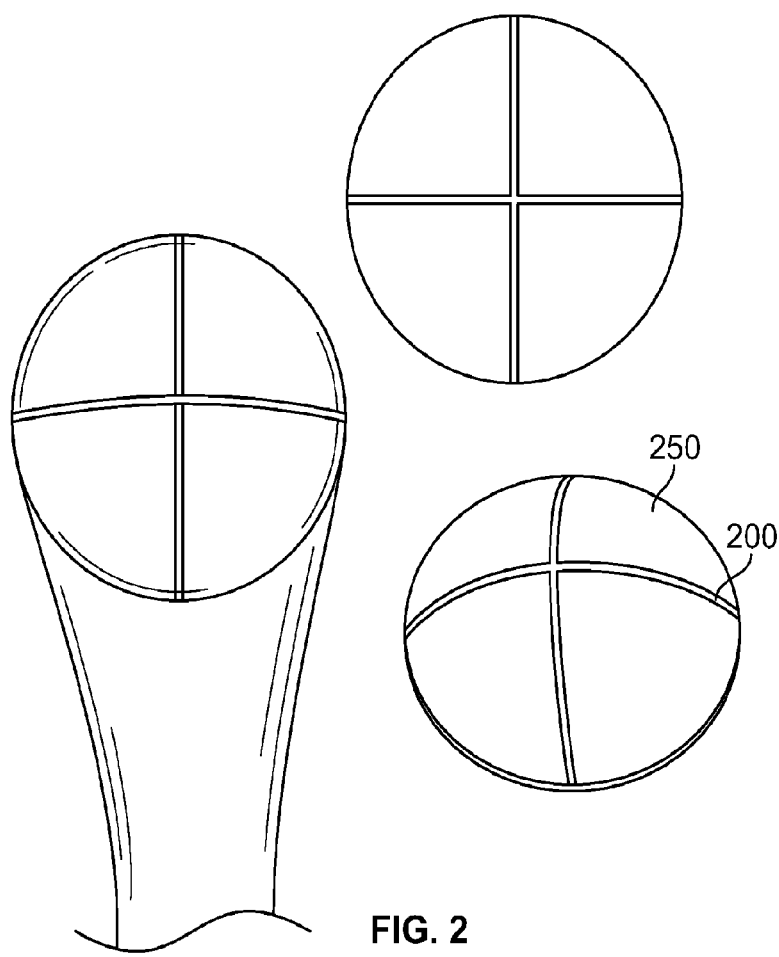
FIG. 2 is a schematic view of an embodiment of an X-Fit prosthesis.
Figure 3:
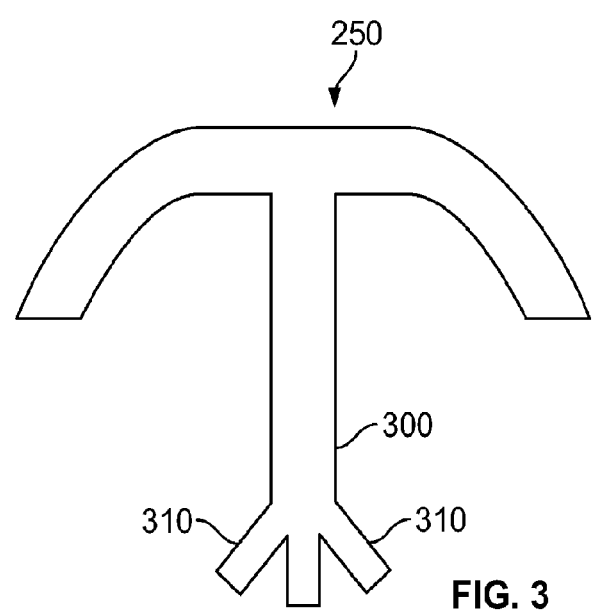
FIG. 3 is a schematic view of an embodiment of a hemispherical implant.

In another embodiment, the multi humeral resurfacing implant is an "X-Fit" prosthesis. An X-Fit prosthesis comprises a hemispherical implant and an X-Fit implant backing. As shown in FIG. 2, the hemispherical implant 250 may have a rounded shape and the X-Fit implant backing may have an X-shape 200. However, the hemispherical implant may be of any appropriate size and shape such as, but not limited to, as shown in FIG. 3. The hemispherical implant may be a bony in-growth backing designed in any appropriate size and shape such as, but not limited to, generally "X"-shaped, generally "Y"-shaped, generally "H"-shaped, generally "K"-shaped, or any variations thereof. The hemispherical implant may also comprise a stem 300 having foldable flanges 310 that are capable of folding outwards to engage a native bone of the humerus. The X-Fit implant backing 200 may be designed in any appropriate size and shape such as, but not limited to, generally "X"-shaped, generally "Y"-shaped, generally "H"-shaped, generally "K"-shaped, or any variations thereof.

As shown in FIGS. 4A and 4B, the hemispherical implant may be X-shaped. As shown in FIG. 4B, the hemispherical implant may be folded 410 together to decrease the size of the implant for implantation, and then be unfolded 420 once positioned where desired. The shape of the hemispherical implant and the X-Fit implant backing may be similar. The shaped bony in-growth backing allows for a similarly shaped X-Fit implant backing to mate with grooves or channels placed into bone of the similar shape or caliber to achieve a "press fit" into the bone. The hemispherical implant or the X-Fit implant backing may be contoured to conform to the shape of the prepared native bone of the humerus.

A short-stemmed humeral implant 500 may include a combination of a base plate 510 and a stem 520 as shown in FIG. 5 and may also be called a stemmed base plate 500. The stemmed base plate 500 may be made of any appropriate material such as metal, tantalum, porous metal, trabecular metal, cobalt chrome, ceramic materials, magnetic metals, titanium, steel, plastic, polymers, polyethylene, bony in-growth material, other suitable materials, and combinations of two or more materials thereof. The stemmed base plate 500 may comprise a bony in-growth surface. In an alternative embodiment, the stemmed base plate 500 comprises a bony in-growth material on its surface while the interior of the stemmed base plate may comprise any appropriate material such as, but not limited to, polished cobalt chrome. The stem portion 520 of the stemmed base plate 500 may be any appropriate size and shape, such as generally cylindrical. The length of the stem portion of the stemmed base plate may range from about 2 mm to about 80 mm. In another embodiment, the length of the stem portion of the stemmed base plate may range from about 5 mm to about 60 mm. In another embodiment, the length of the stem portion of the stemmed base plate may range from about 10 mm to about 40 mm.

The diameter of the stem portion of the stemmed base plate may range from about 1 mm to about 50 mm. In another embodiment, the diameter of the stem portion of the stemmed base plate may range from about 2 mm to about 35 mm. In another embodiment, the diameter of the stem portion of the stemmed base plate may range from about 4 mm to about 15 mm. The stemmed base plate may be placed into the metaphyseal bone of the humerus 570 as shown in FIG. 5 and does not traverse or proceed deeply and distally into the canal of the shaft of the humerus.

The stemmed base plate may have a female end into which a male stemmed humeral ball implant may mate in any fashion such as, but not limited to, a taper-lock fashion. In an alternative embodiment, the stemmed base plate includes a male tower onto which a female shaped humeral ball implant may mate in any fashion such as, but not limited to, a taper-lock fashion.

The stemmed based plate 500 may be locked into place with healing as the bone interdigitates. The stemmed base plate may further comprise a folding mechanism at the tip of the stem. The folding mechanism may comprise flanges 110 as shown in FIG. 1A. The folding mechanism may be any suitable size and shape, such as, but not limited to, petal-like, X-like, cross-like. As shown by a non-limiting example in FIG. 1A, the folding mechanism may be unfolded by means of a screw device 120 engaging flanges 110 into the native bone which further secures the short stemmed humeral implant.

One advantage of a stemmed base plate having a bony in-growth surface on the outer aspects, such as the areas that may contact the native bone, is that the stemmed base plate having a bony in-growth surface allows the stemmed base plate to integrate and fit tightly with the native bone.

The glenoid implant may be a standard keeled or pegged implant, metal backed bony in-growth pegged implant, or a stemmed/pegged and inset device. The glenoid implant may be made of any appropriate material such as metal, tantalum, porous metal, trabecular metal, cobalt chrome, ceramic materials, magnetic metals, titanium, steel, plastic, polymers, polyethylene, bony in-growth material, other suitable materials, and combinations of two or more materials thereof.

Figure 21A:
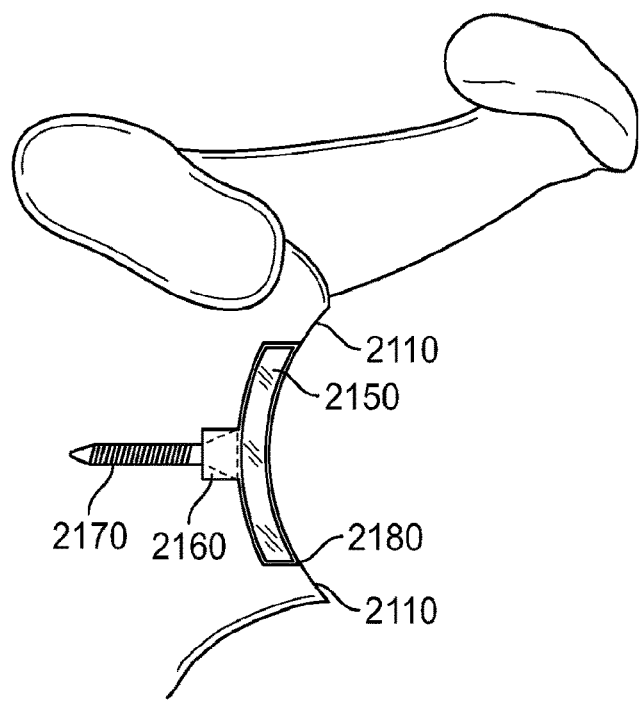
FIG. 21A is a perspective view of an embodiment of a glenoid implant.
Figure 21B:
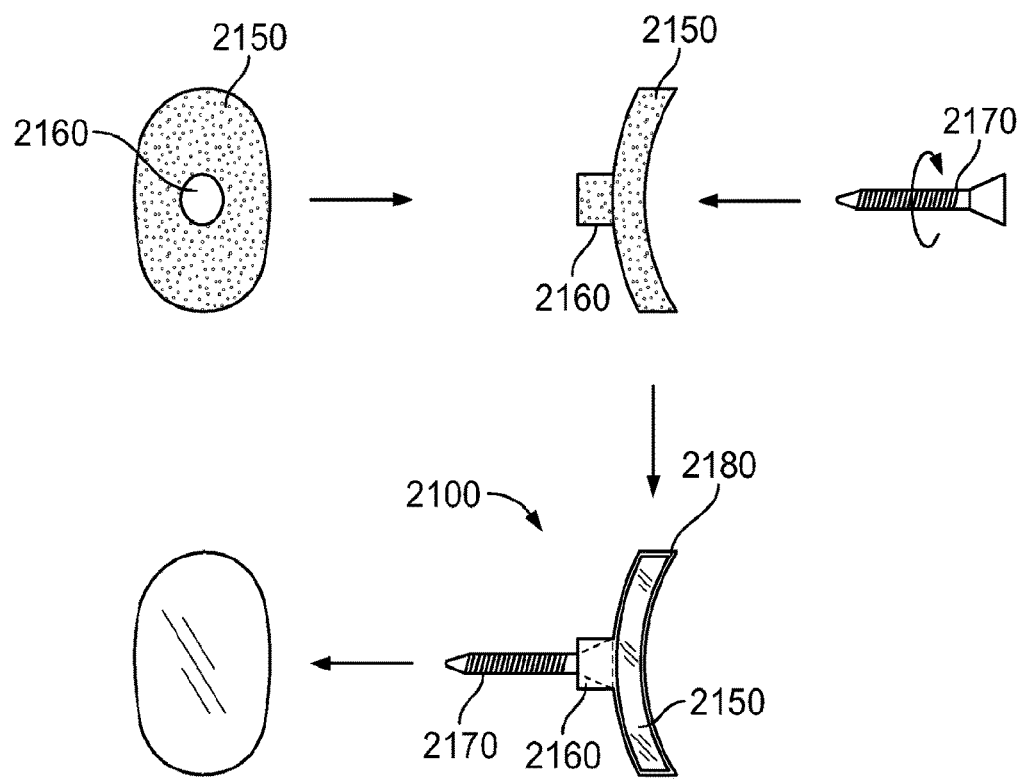
FIG. 21B is a schematic view of an embodiment of a glenoid implant.

The glenoid implant may comprise a metal, polyethylene composite. As shown in FIGS. 21A and 21B, the glenoid implant 2100 may comprise a shell 2150 that may be comprised of any metal such as tantalum, porous metal, trabecular metal, cobalt chrome, magnetic metals, titanium, any alloy comprised thereof or other metals. The metal shell 2150 may be coated with a porous coating and may have a central hollow peg 2160 that may be press fit into bone. A screw 2170 may then by placed through the hollow peg 2160 to further engage bone. Expanding petals or flanges may also be used to engage the bone. As shown in FIG. 21A, the glenoid implant 2100 may be placed substantially flush with the surface bone of the glenoid 2110. The metal shell 2150 may be placed substantially flush with the surface bone of the glenoid 2110. In general, the glenoid implant 2100 is typically placed substantially flush with the glenoid 2110 after the glenoid has been prepared by template/router devices. In another embodiment, the glenoid implant 2100 may comprise a metal shell 2150 having a polyethylene liner snap 2180 placed onto the metal shell 2150 as shown in FIG. 21B. After the glenoid implant 2100 is placed substantially flush with the surface bone of the glenoid a polyethylene liner snap 2180 may be placed onto the metal shell 2150. A polyethylene liner snap 2180 may be placed onto the metal shell 2150 before the glenoid implant 2100 is placed substantially with the surface bone of the glenoid.

The standard keeled or pegged implant may be any standard keeled implant. The metal backed bony in-growth pegged implant may be any metal backed bony in-growth pegged implant.

Figure 6:
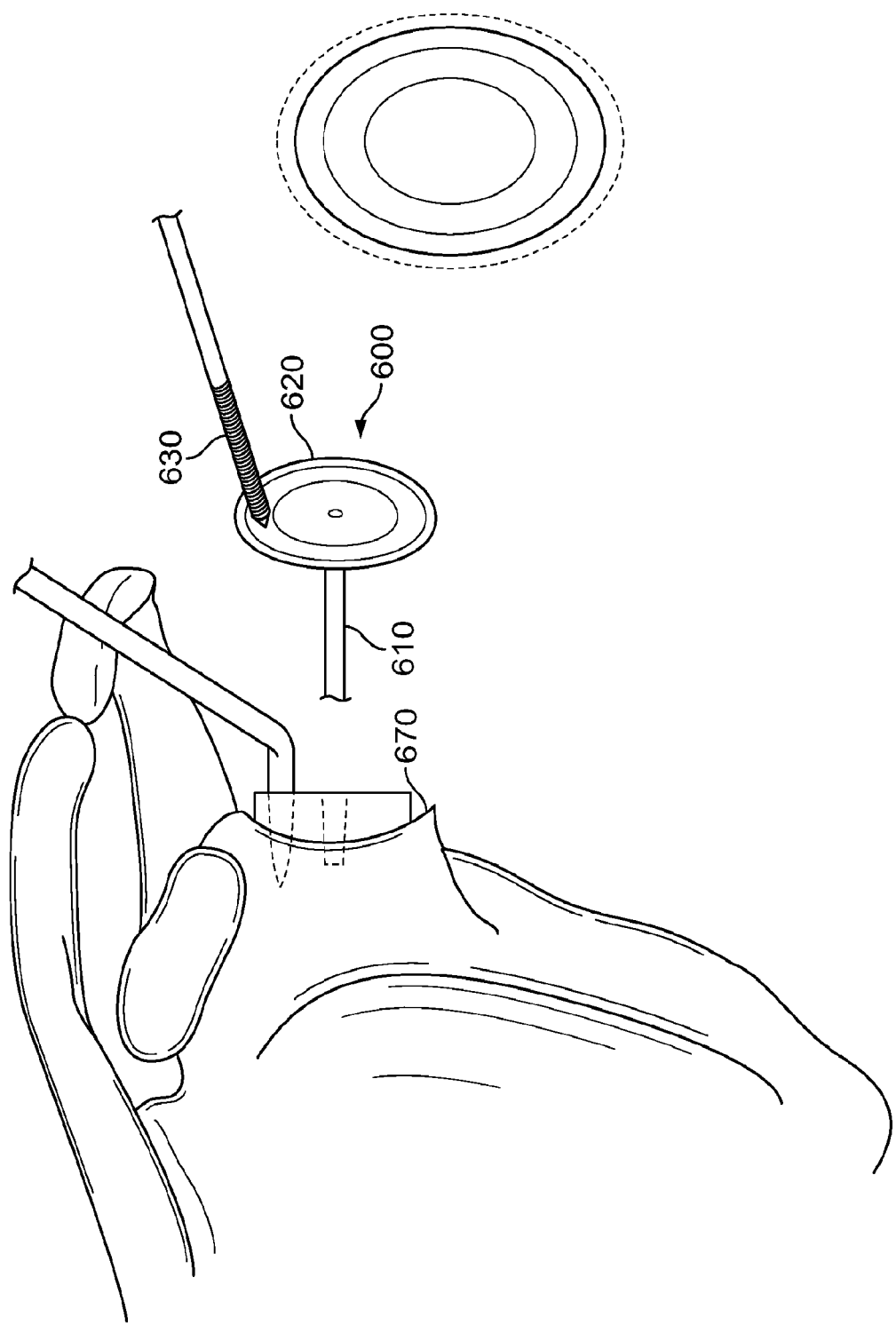
FIG. 6 is a perspective view of an embodiment of a stemmed/pegged inset device.

In another embodiment, the glenoid implant may be a stemmed/pegged inset device 600 as shown in FIG. 6. In use, the stemmed/pegged inset 600 device is flush with the native bone of the glenoid 670. The stemmed/pegged inset device may be made of any appropriate material such as metal, tantalum, porous metal, trabecular metal, cobalt chrome, ceramic materials, magnetic metals, titanium, steel, plastic, polymers, polyethylene, bony in-growth material, other suitable materials, and combinations of two or more materials thereof.

The stemmed/pegged inset device 600 includes a central peg 610 and flanges extending outward from the central peg 610. The stemmed/pegged inset device may comprise bony in-growth material such as, but not limited to, a metal. The stemmed/pegged inset device may further comprise a base plate 620. The base plate may be comprised of metal, plastic, polyethylene, steel, trabecular metal, cobalt chrome, titanium, polymers, bony in-growth material or other suitable materials. The base plate 620 may be mated to the native bone via at least one of bone in-growth coating and locking screws 630. A contact or articulating surface comprised of polyethylene, or other suitable materials, may be snapped or press fit onto the base plate to become the surface that articulates with the ball.

Figure 22:
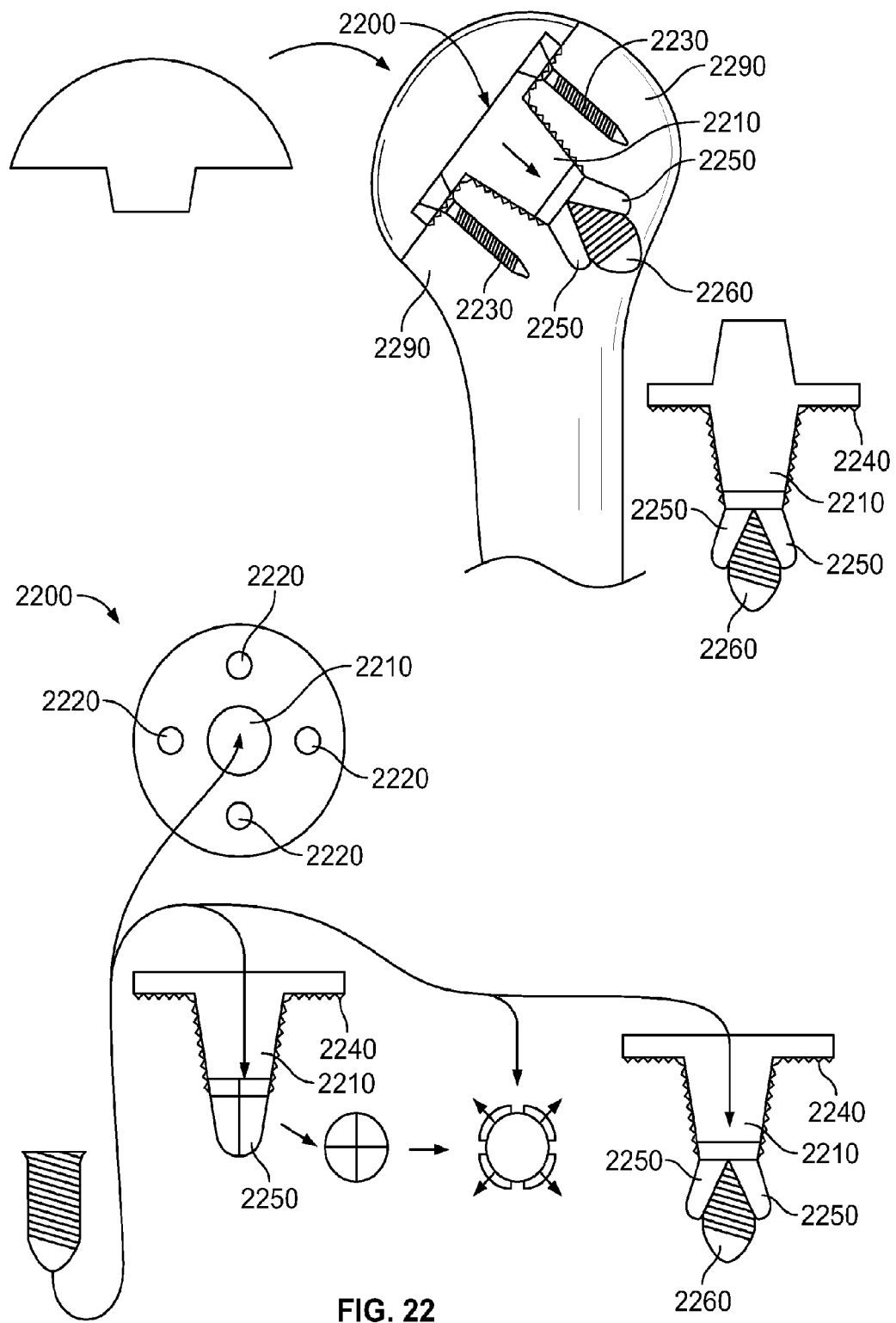
FIG. 22 is a schematic view of an embodiment of a stemmed/pegged inset device.

In another embodiment, a stemmed/pegged inset device 2200, as shown in FIG. 22, comprises a central peg 2210 having flanges 2250 that extend outward and/or downward when an interface screw 2260 is deployed. The flanges 2250, upon being deployed by the interface screw 2260 engage the humeral head 2290 to provide stability. The stemmed/pegged inset device 2200 may also include at least one or a plurality of openings 2220 which may receive engaging devices 2230, such as, but not limited to, screws, to further engage the humeral bone to provide added stability. The stemmed/pegged inset device may also be coated with a porous coating 2240.

The improvements provided by stemmed/pegged inset device 2200 as described above helps allow the stemmed/pegged inset device 2200 to be placed flush and inlayed with the native bone. In one embodiment, as opposed to an implant device comprising mostly polymer materials, the flush inlayed stemmed/pegged inset device may comprise a metal backing with a polymer-type material that may snap on to the metal backing. The flush, inlayed stemmed/pegged inset device may improve the biomechanics of the shoulder arthroplasty such that loosening of the glenoid component is avoided and longevity is improved for the shoulder arthroplasty.

The implantation surgical devices comprise devices used for the preparation of the shoulder area for the insertion of the humeral implant and/or the glenoid implant, devices for inserting the humeral implant and/or the glenoid implant, and devices for attaching/locking the humeral implant and/or the glenoid implant into a desired location.

The preparation of the shoulder area for a humeral resurfacing implant may require spherical milling or grating of the bone such that the bone achieves a spherical type of shape over which, on to which, or into which an implant, such as the humeral resurfacing implant, may be inserted.

Figure 7C:
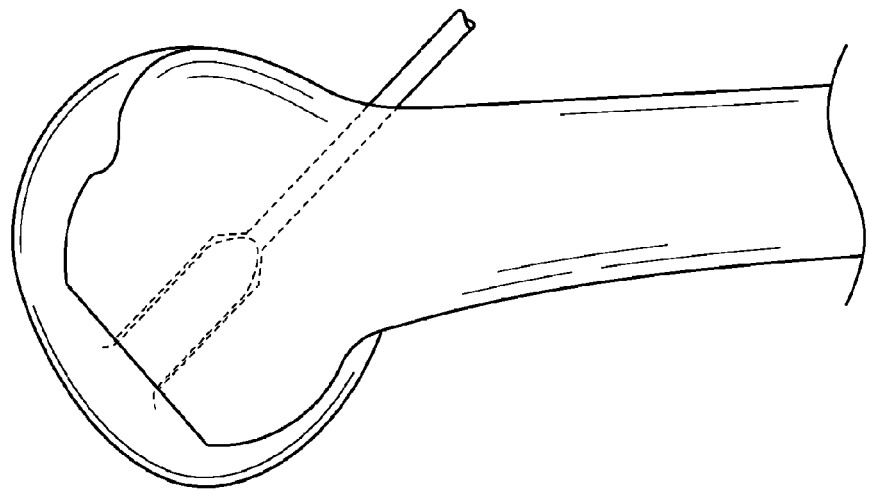
FIG. 7C is a side view of an embodiment of a humerus after a reaming structure has been removed.
Figure 7B:
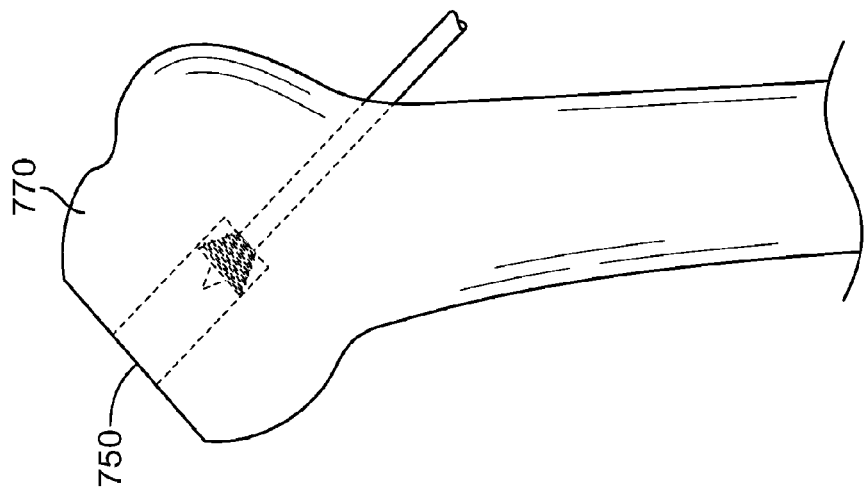
FIG. 7B is a side view of an embodiment of a reaming structure inserted in a humerus.
Figure 7A:
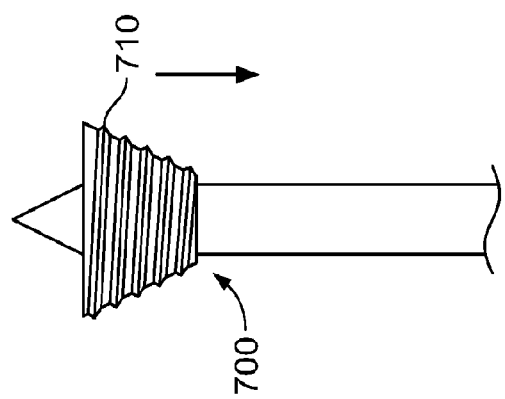
FIG. 7A is a perspective view of an embodiment of a reaming structure.

As shown in FIGS. 7A, 7B, and 7C, a reaming structure 700, such as, but not limited to, a metal shaft, wire, or pin, may be used for preparation of the shoulder area for insertion of a humeral resurfacing implant. In a non-limiting example, the reaming structure may be threaded 710 as shown in FIG. 7A. As shown in FIG. 7A, the radius of the threaded portion 710 of the reaming structure may increase or decrease along the longitudinal distance of the reaming structure. The reaming structure 700 may be placed through the humerus 770 in a retrograde fashion, beginning with a small stab through the skin of the upper outer arm and traversing into the bone of the humerus such that the reaming structure 700 achieves a position near the center of the Humeral Head (Ball) of the shoulder joint 750.

Achieving the correct position of the reaming structure 700 may also be achieved by either: 1) Placement of a patient-specific, CT or MRI determined/guided, registering template onto the bone of the humerus to guide the reaming structure 700 into the correct position near the center of the humeral head, or 2) Placement of a reaming structure 700 "ACL" type of guide onto the ball and shaft of the humerus to guide the reaming structure 700 into the correct position. In addition, live radiography may also be used to assist and confirm positioning of the reaming structure 700.

Figure 8:
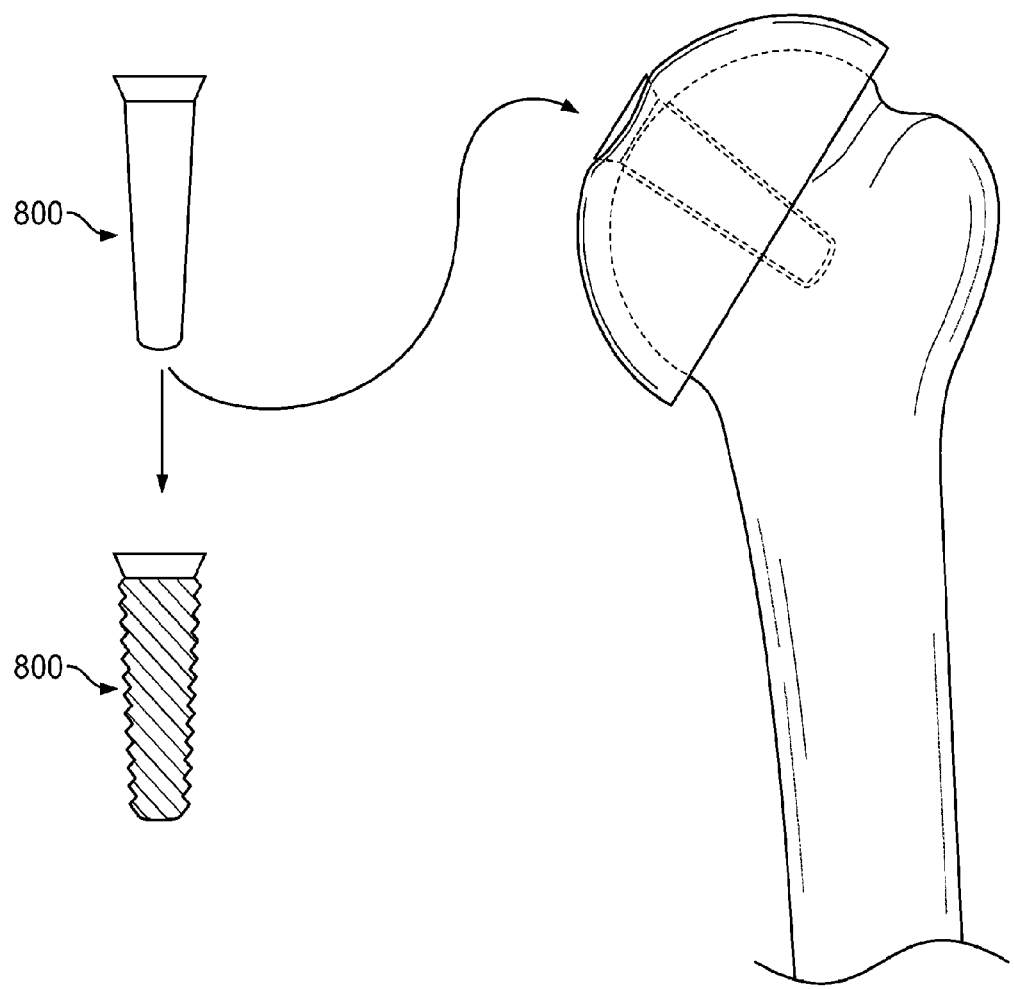
FIG. 8 is a schematic view of an embodiment of a threaded screw.

Preparation of the shoulder area for insertion of a humeral resurfacing implant may be achieved by reaming or grating of a bone into the desired shape in a retrograde fashion. This may include increasing the size of reaming, grating, or milling devices to mate with the reaming structure 700 such that increasing diameter and depth of humeral head bone may be removed and shaped to accept an implant such as, but not limited to, a humeral implant or a glenoid implant. The reaming, grating, or milling devices 800 may be placed antegrade via arthroscopic incisions or portals and mate via screw/thread mechanism, as shown in FIG. 8, with the reaming structure and be pulled while spinning at drill speed to achieve contact with bone and remove bone.

Figures 9A, 9B:
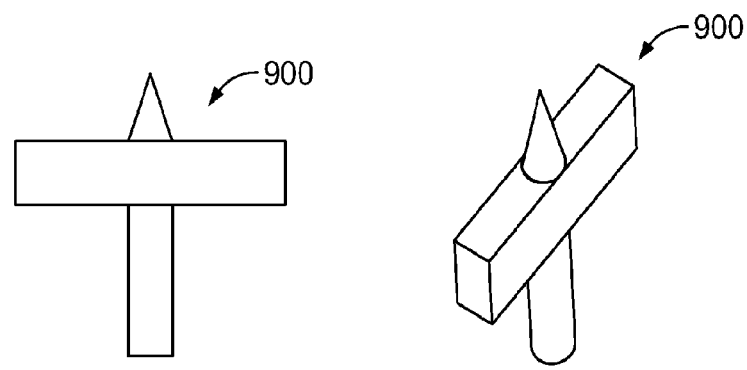
FIG. 9A is a schematic view of an embodiment of a flat reamer.
FIG. 9B is a perspective view of an embodiment of a flat reamer.

In another embodiment, flat reaming 900 and low profile 1000 reaming devices may be used. Unlike previous reaming devices, the flat and low profile reaming devices, as shown in FIGS. 9A, 9B, 10A, and 10B, allow for passage through small arthroscopic incisions. As shown in FIGS. 9C and 10C, the flat reaming device 900 and low profile reaming device 1000 may be circular spun in a humerus 950/1050.

In preparation of insertion of an X-Fit prosthesis, after spherical reaming, a metal template may be used for the preparation of the shoulder area for insertion of a humeral resurfacing implant. The metal template may be placed onto the native bone designed in any appropriate size and shape, such as, but not limited to, an "X", that will allow for an angled reamer, mill, router, or other devices to prepare the native humerus bone into the desired appropriate female size and shape to allow for the implant of the desired appropriate male size and shape to insert at time of final implant insertion The preparation of the shoulder area for a short-stemmed humeral implant may require a resection of the bone of the humerus(ball) in such a location as is performed in open surgery just below the spherical ball in the anatomical location that is termed the "anatomical neck" of the humerus. This will provide the primary basic bone preparation onto which, or into which various options for humeral implants may be positioned and fixed to the native bone of the humerus.

Figure 11:
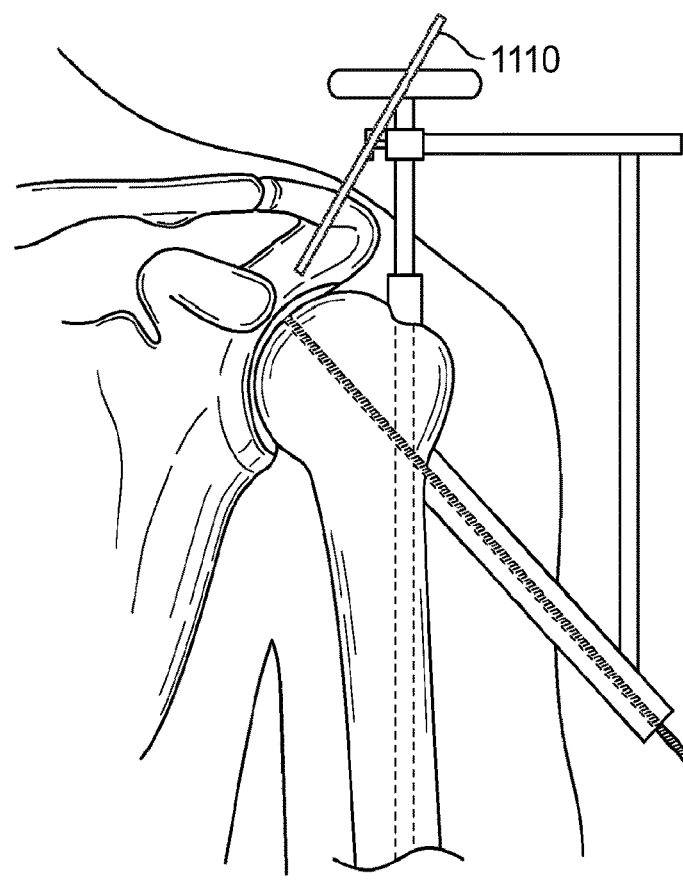
FIG. 11 is a schematic view of an embodiment of preparation of a humerus for an implant.
Figure 12:
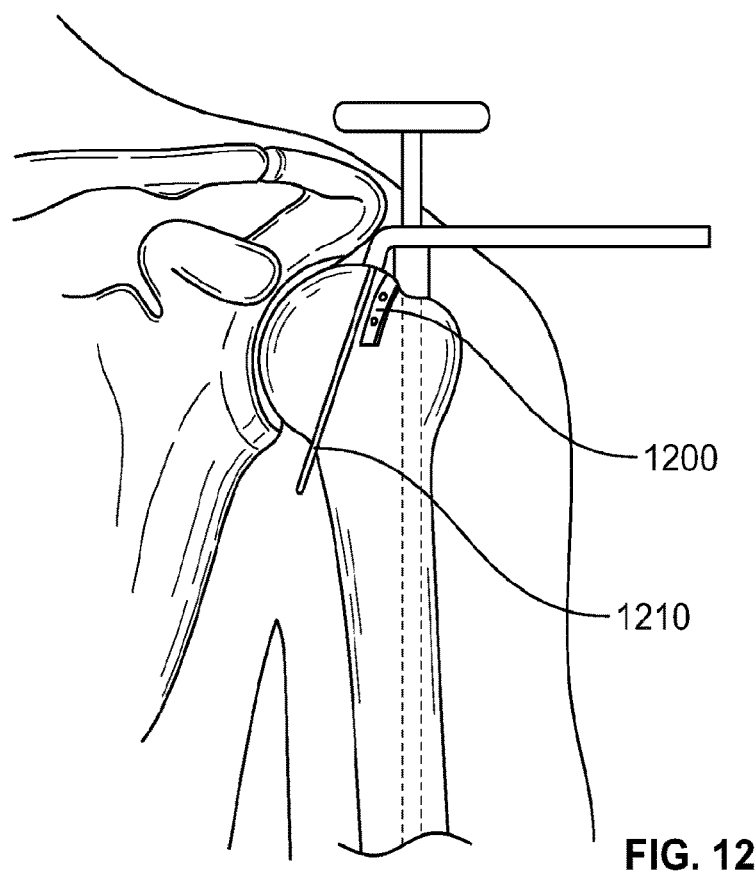
FIG. 12 is a schematic view of an embodiment of preparation of a humerus for an implant.

As shown in FIGS. 11 and 12, preparation of the humerus for a humeral implant, such as, but not limited to, a short-stemmed humeral implant, may be achieved for the primary bone resection by using a CT or MRI guided template 1110 placed onto native bone that will hold a small cutting jig 1200 to allow placement of a small width saw through an arthroscopic incision or passage 1210 to allow for cutting of the humeral bone along the "anatomical neck."

Figure 13:
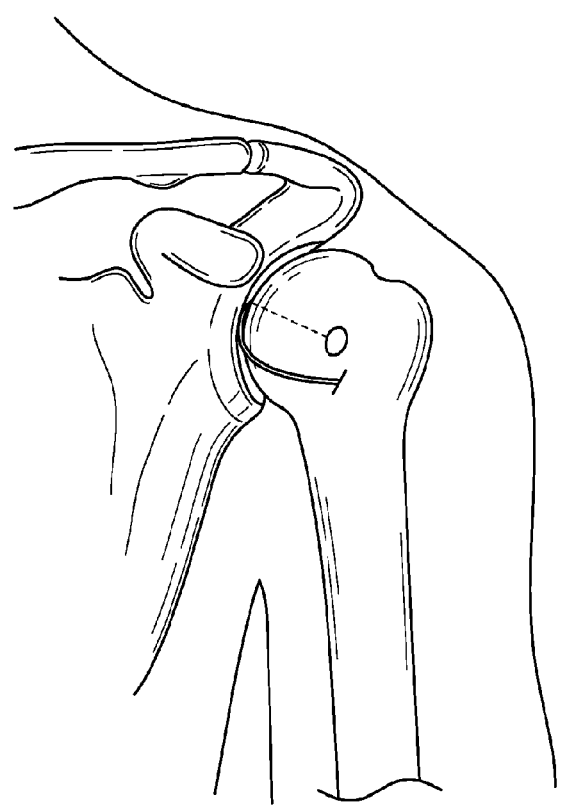
FIG. 13 is a schematic view of an embodiment of preparation of a humerus for a humeral implant using a modified variation of an ACL guide.
Figure 14:
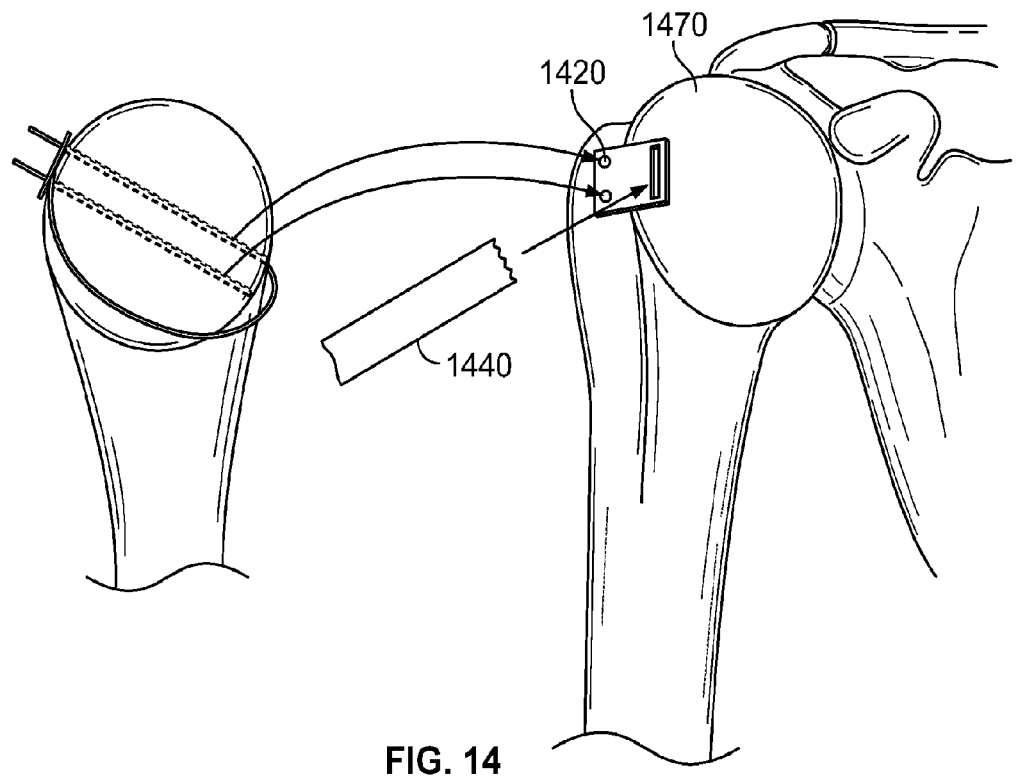
FIG. 14 is a schematic view of an embodiment of preparation of a humerus for a humeral implant using a modified variation of an ACL guide.
Figure 15:
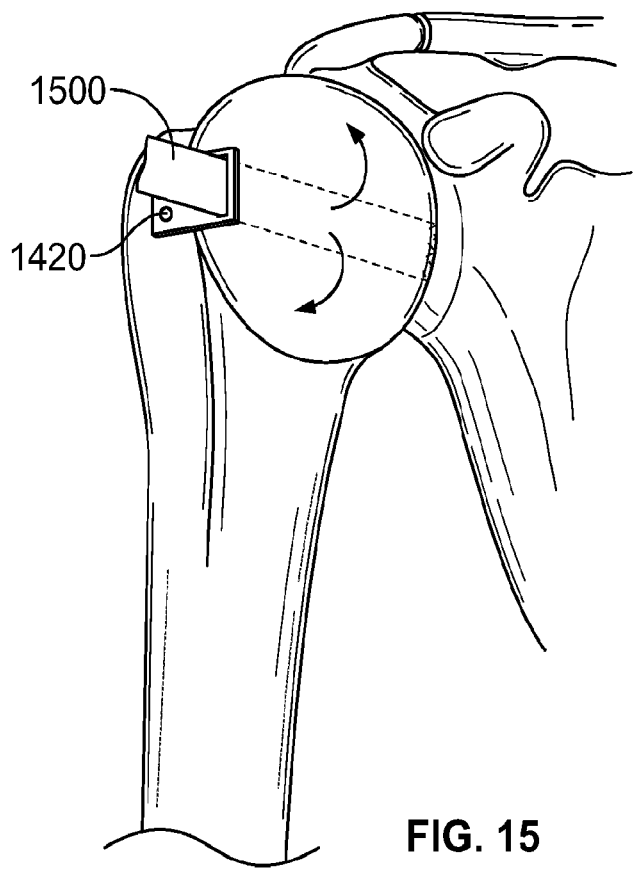
FIG. 15 is a schematic view of an embodiment of preparation of a humerus for a humeral implant using a modified variation of an ACL guide.

The preparation of the humerus for a humeral implant, such as, but not limited to, a short-stemmed humeral implant, may be achieved by using a modified variation of an ACL guide, as shown in FIGS. 13, 14 and 15, that fits through an arthroscopic portal into the joint and aim from one side of the humeral ball 1470 to the other and allow for guide pins 1420 to be placed over which a cutting block or thin free handed saw 1440 may be placed to facilitate the cutting of the native bone in the correct location. The guide pins may be threaded. A folded in-growth stem 1500 may be inserted into the opening before being unfolded as shown in FIG. 15.

Figure 16:
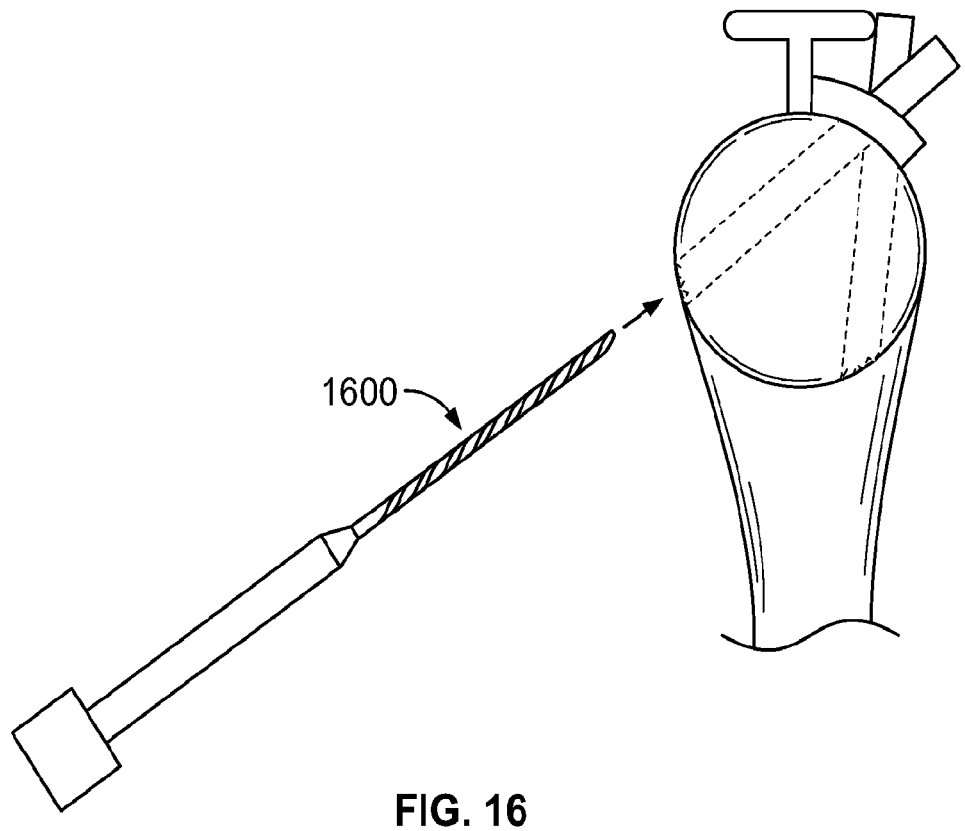
FIG. 16 is a perspective view of an embodiment of a milling or router drill.
Figure 17:
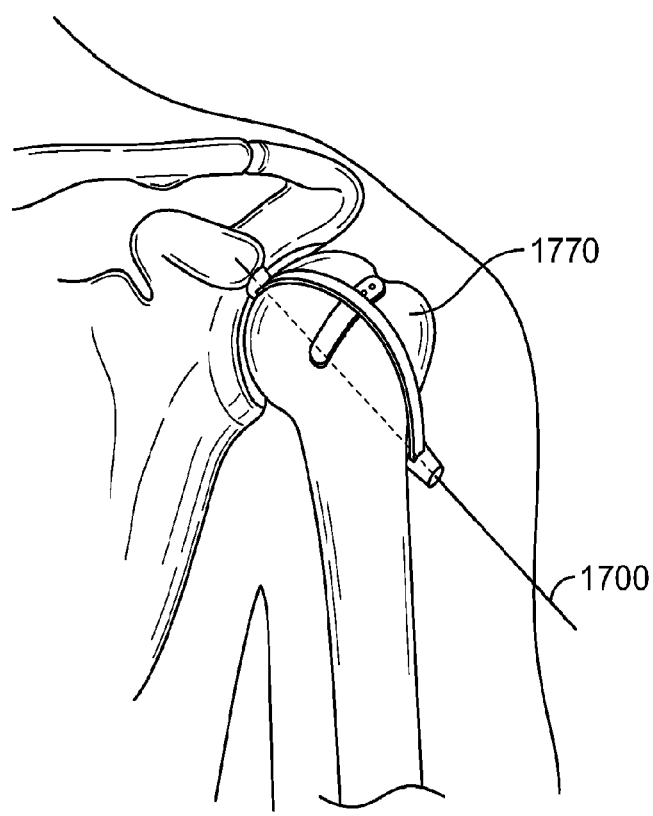
FIG. 17 is a schematic view of an embodiment of secondary preparation of a humerus.
Figure 18:
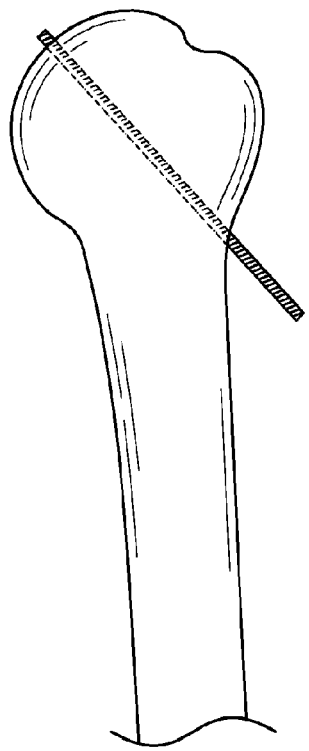
FIG. 18 is a schematic view of an embodiment of secondary preparation of a humerus.
Figure 19:
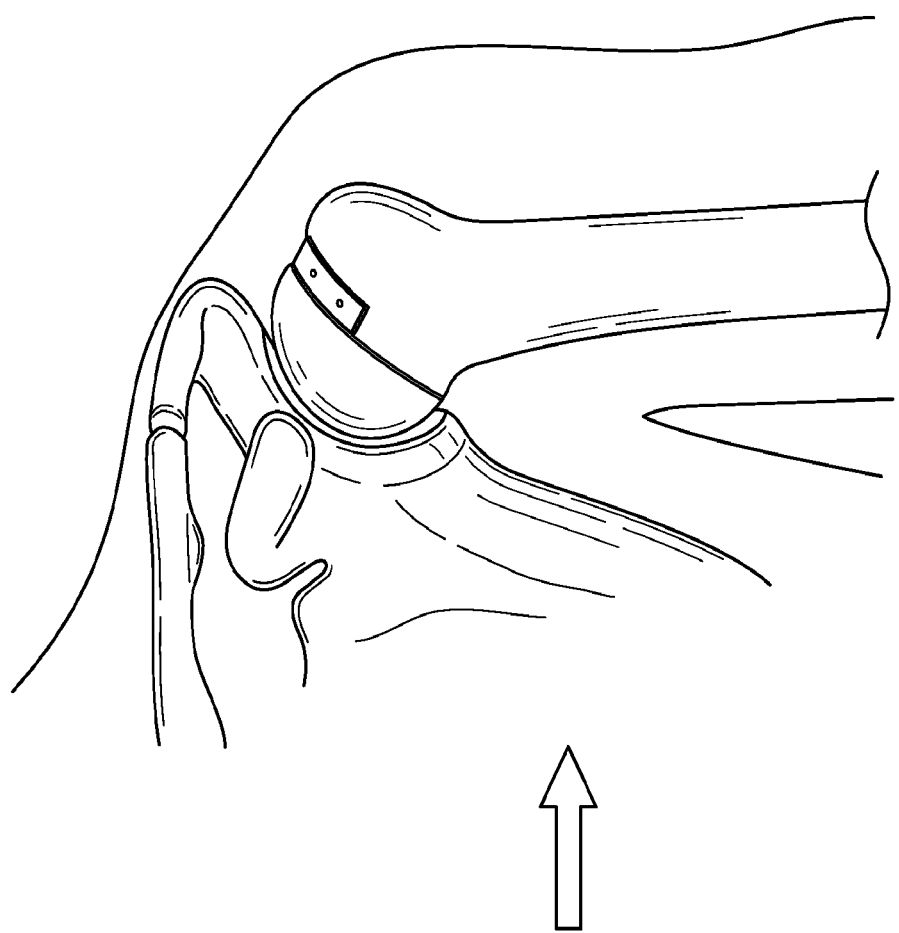
FIG. 19 is a schematic view of an embodiment of secondary preparation of a humerus.
Figure 19:
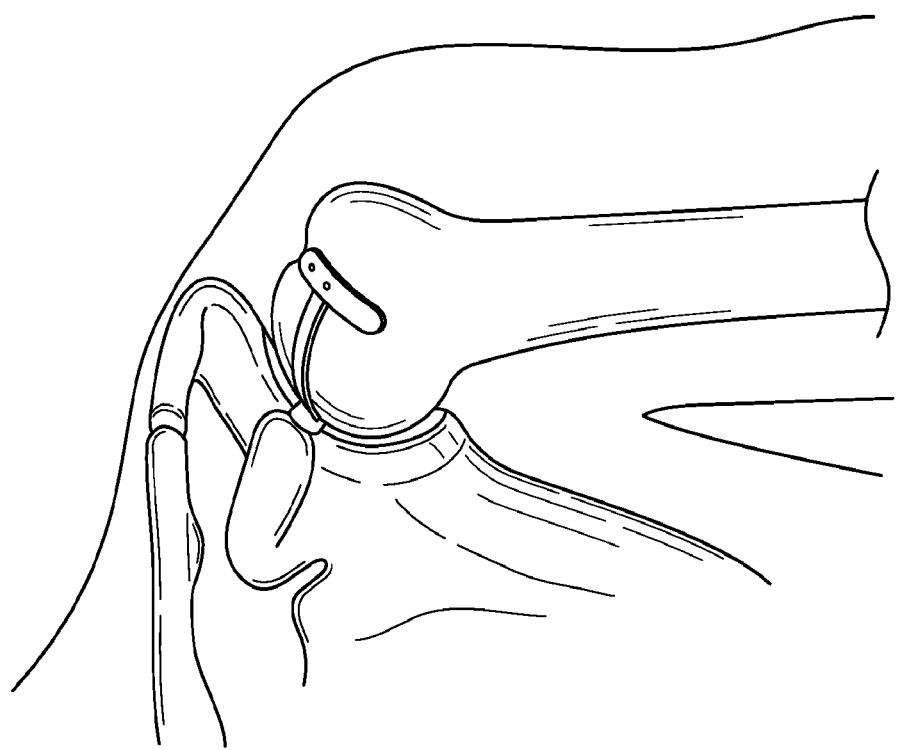
Figure 20:
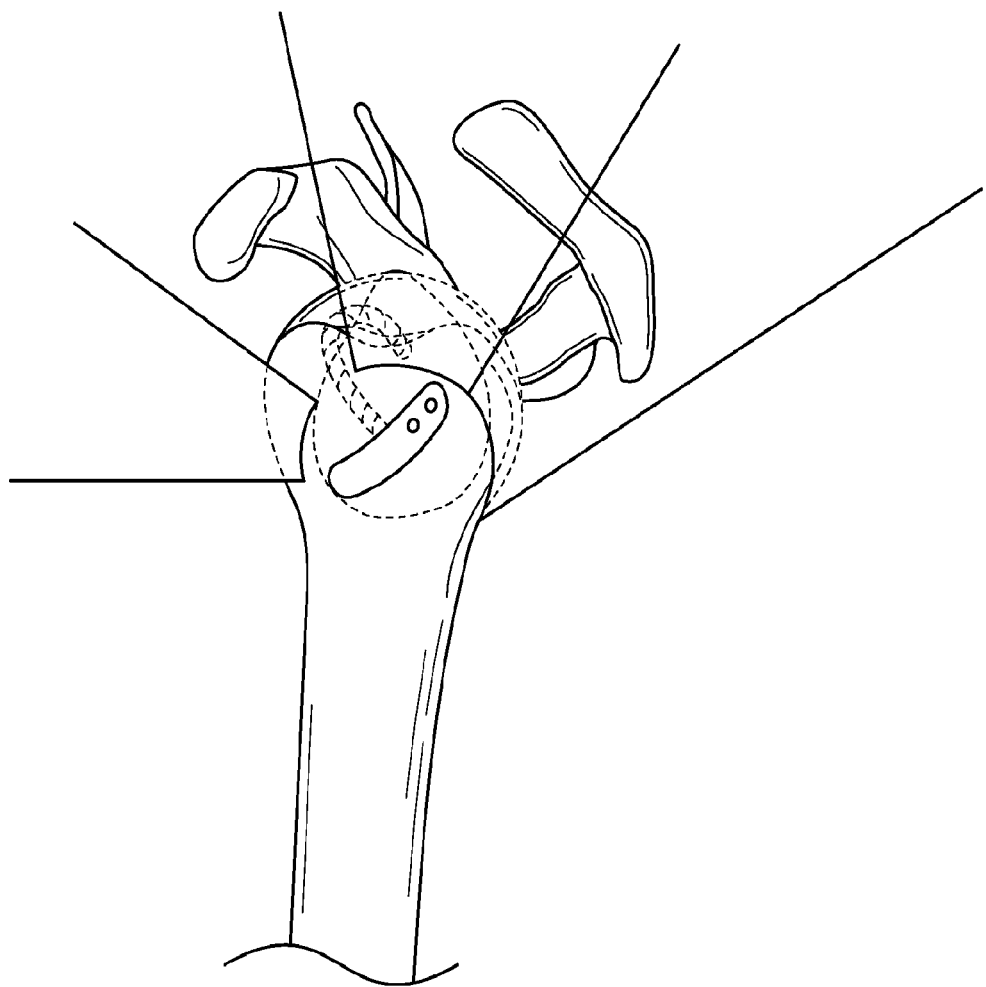
FIG. 20 is a schematic view of an embodiment of secondary preparation of the humerus.

As shown in FIG. 16, the cut itself may also be made by using a milling or router type of drill 1600 that may be placed through an appropriately positioned cutting block or guide as above such that this very small diameter and low profile drill/router/mill may effectuate the cutting of bone without need for an actual saw blade that is more high profile.

Once the resection of bone is achieved the resected bone may be broken into smaller pieces with a saw/drill/mill/router or other known devices and removed in a piece-meal fashion through the arthroscopic portals.

Secondary bone preparation may be made either in an antegrade fashion through the portals or in a retrograde (trans-humeral) fashion. As shown in FIGS. 17-20, a channel into bone may either be made antegrade over a guide wire 1700 with a bone punch to accept the stemmed base plate, or a channel may be achieved via a retrograde reamer that will mate with a guide pin placed through the bone of the humerus 1770. The stemmed base plate may be impacted into this channel by either an antegrade pushing device or retrograde pulling device. In addition, when an expanding lead design is used for the short-stemmed humeral implant the stemmed base plate may then be further fixed as desired.

Low profile, and angulated or articulated, router or mill type devices that will mill or router a trough via a template applied to bone may be used such that a glenoid implant may be introduced flush to the surface. The placement of a glenoid implant flush will allow the implant itself to be of a thickness that is less than existing implants to prevent a rocking horse effect and thus loosening of the implant.

The shoulder area may be prepared for a standard keeled/pegged or metal backed pegged/ingrowth glenoid implant by reamers. The reamers may be low profile or flat reamers, as shown in FIGS. 9A, 9B, 10A, and 10B, capable of mating with a trans-humeral placed shaft or reamer pin to achieve reaming or grating of the glenoid bone in an antegrade fashion. The reamers may be flat and linear, as shown in FIGS. 9A, 9B, 10A, and 10B, but not spherical or hemispherical, to allow for passage through arthroscopic portals. Once the flat or low profile reamers mate with the shaft or pin, the desired circular reaming preparation of the bone may be achieved by circular spinning as shown in FIG. 9C. Alternatively, the flat or low profile reamers may be introduced through an arthroscopic portal with an angled reaming shaft and with increasing diameters to reach the appropriate size and depth of reaming. Smaller profile and thin templates capable of fitting through arthroscopic portals may be used in conjunction with trans-humeral or arthroscopic portals to drill keels or pegs.

The shoulder area may be prepared for insertion of a stemmed/pegged and inset device implant. The preparation of the native bone would be a circular template of varying sizes to match the native bone onto which or through which an angled drill/reamer or mill/router may be placed to follow a circular path and drill to a depth of about 2-3 millimeters. This would be followed by smaller diameter circles to complete a full reaming of an inset channel in the bone into which the stemmed/pegged and inset device implant may be seated. The circular reaming template approach may also be MRI or CT guided. The circular reaming template approach may also be a patient specific template to guide correct bony cutting. A template may be seated into a central peg hole that may be created via an angled drill through arthroscopic portals or through a channel in the humerus (trans-humeral).

In another embodiment, the humeral resurfacing implant is a singular humeral resurfacing implant. The singular humeral resurfacing implant may be made of any appropriate material such as metal, tantalum, porous metal, trabecular metal, cobalt chrome, ceramic materials, magnetic metals, titanium, steel, plastic, polymers, polyethylene, bony in-growth material, other suitable materials, and combinations of two or more materials thereof.

Figure 23A:
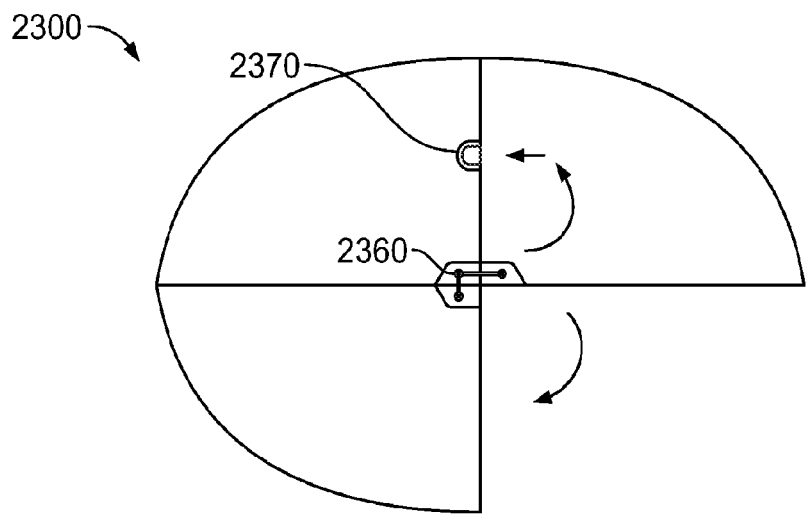
FIG. 23A is a schematic view of an embodiment of a singular humeral resurfacing implant.
Figure 23B:
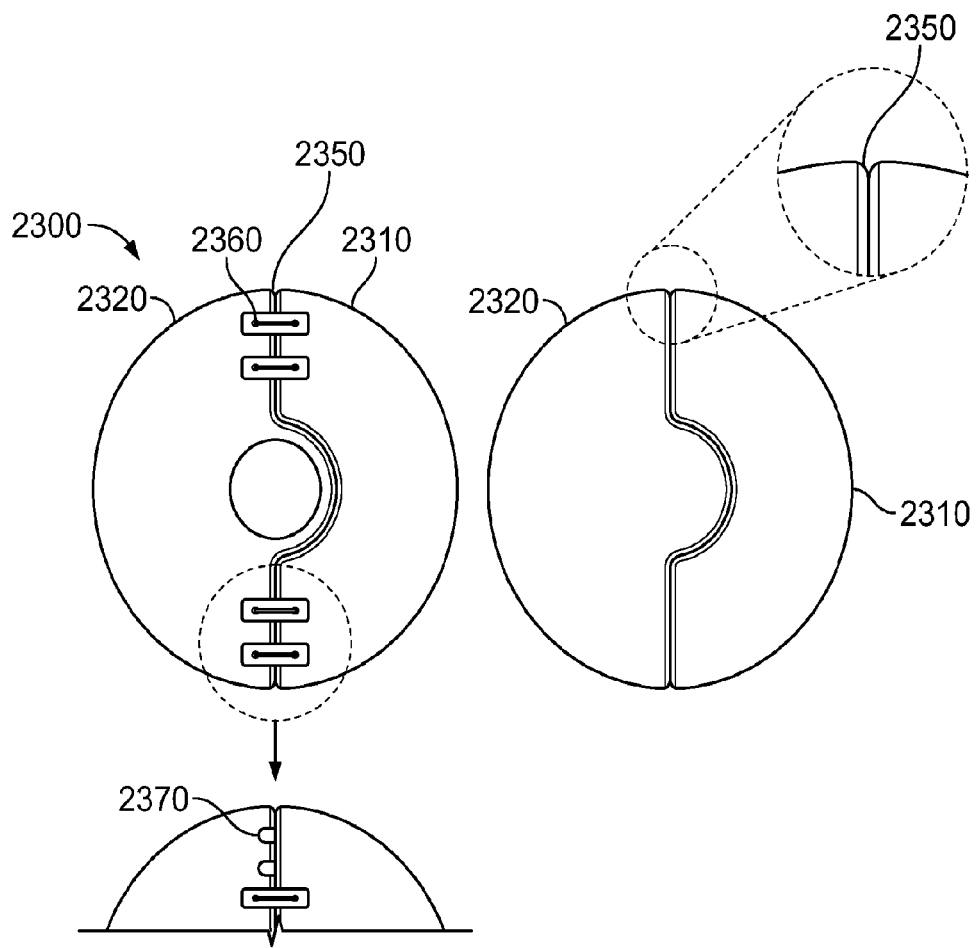
FIG. 23B is a schematic view of FIG. 23A in a deployed orientation.

The singular humeral resurfacing implant 2300 may be a bone in-growth backed implant and may be folded towards the center of the singular humeral resurfacing implant as shown in FIGS. 23A and 23B. The singular humeral resurfacing implant may be capable of being folded. The singular humeral resurfacing implant is in the undeployed state when the folds are folded towards the center. When the folds are deployed, the folds 2310, 2320 may extend outward and downward. The singular humeral resurfacing implant folds may be deployed via a set screw mechanism. The set screw mechanism may be employed or engaged in an antegrade or retrograde fashion. The singular humeral resurfacing implant folds may have slightly rounded edges 2350, as shown in FIG. 23B. The slightly rounded edges of the folds help prevent wear of opposing articulating implants, and allows for the singular humeral resurfacing implant to be placed through a small passage or incision in to the joint while the singular humeral resurfacing implant remains folded.

When deployed, the folds 2310, 2320 may be locked in a deployed position by any known locking means such as, but not limited to, hinges 2360 and snaplocks 2370. The locking means lock the folds in a desired position after the folds are deployed.

Figure 24A:
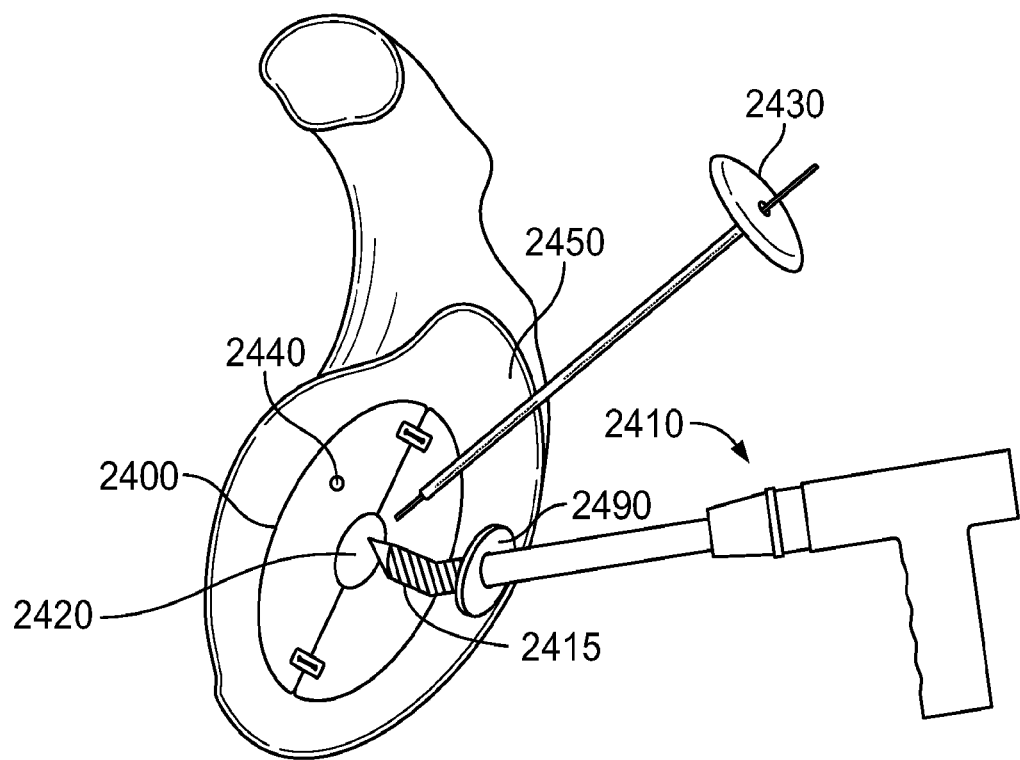
FIG. 24A is a schematic view of an embodiment of a template and a router/mill device.

FIG. 24A shows a template and router/mill type device. While similar to a high speed burr, this router/mill device 2410 is specifically created to mate with channels/windows 2470 in the template 2400 to guide it to desired circumferences and depths to mill out a space of the glenoid 2450 for the glenoid components. The router/mill device may have to be angled 2415, as shown in FIG. 24A, instead of straight and comprise of a generally lower profile to fit through arthroscopic cannulas. The handle 2430 may be cannulated to allow pin placement through the handle 2430 and temporary pin fixation while reaming and routering. The template 2400 may comprise an aperture 2440 to allow for pin placement through the aperture 2440 to provide greater stability. The aperture 2440 may located as shown in FIG. 24A. However, the aperture 2440 may be located in any location on the template 2400. The template itself may be placed into the joint with a shaft/handle attached to it. The template may also fold in the middle to get into the joint. The template 2400 may be provisionally pinned into place with a wire. The router/mill device may comprise a collar 2490 to prevent the router/mill device from going past a desired depth.

The template may further comprise a central peg 2420 about the same size of the implanted device. The central peg 2420 would allow for stability of the template during milling and allow a wire to pin the template in place. This would require a primary template first that simply locates the location of the central starting hole, which would be drilled with an articulated or angled or flexible shaft drill bit.

Figure 24B:
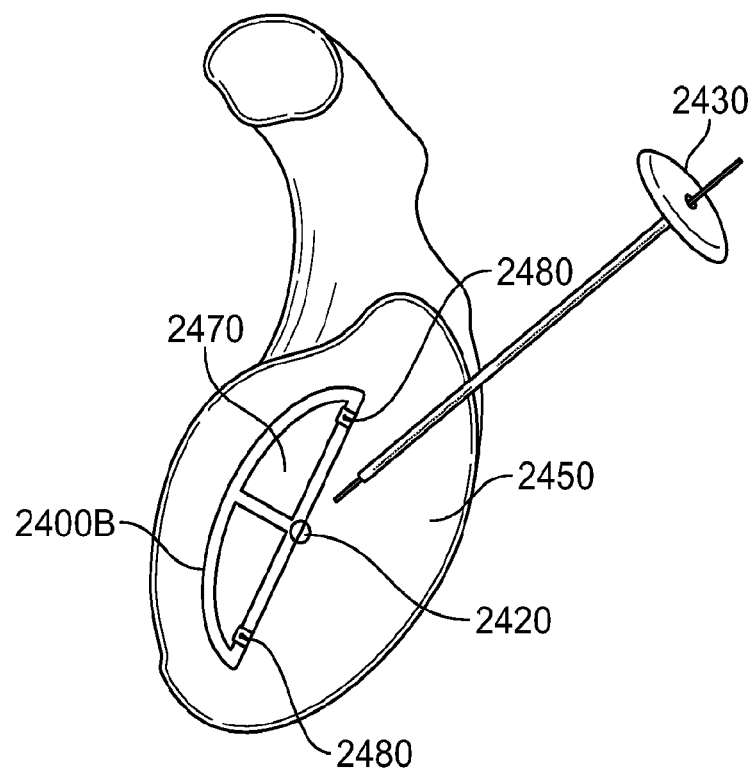
FIG. 24B-1 is a schematic and side view of an embodiment of a folded template engaging a bone.
Figure 1:
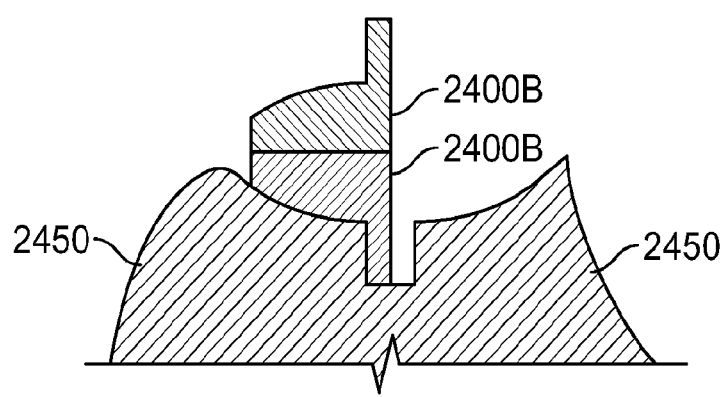

FIG. 24B-1 shows a template 2400B in a folded state being introduced into a shoulder joint. The central peg 2420 may also be folded for entry. After the template 2400B enters the desired area, the template 2400B and central peg 2420 will unfold and engage the glenoid, as shown in FIG. 24B-2. The template may fold or unfold by use of hinges 2480. However, the template may fold or unfold by other means. The unfolded template 2400B may comprise windows 2470, as shown in FIG. 24B-2, that are open to allow bone to be routered out with a collared router. In a non-limiting embodiment, the template 2400B may have four windows where the four windows are approximately equal in size. However, the template may have as many windows as desired such as, but not limited to, two, three, four, five, six, seven, eight, nine, or ten. The router/mill device may be used in conjunction with the aperture 2440.

After the template is placed in the desired location as described above, the remaining bone needs to be routered. Unlike the template in FIGS. 24B-1 and 24B-2 which has windows, the template in FIGS. 24C-1 and 24C-2, comprises a template with a t-shaped 2495 opening when unfolded. The opened t-shape template 2400C may comprise metal, tantalum, porous metal, trabecular metal, cobalt chrome, ceramic materials, magnetic metals, titanium, steel, plastic, polymers, polyethylene, bony in-growth material, other suitable materials, and combinations of two or more materials thereof.

Figures 2, 24B:
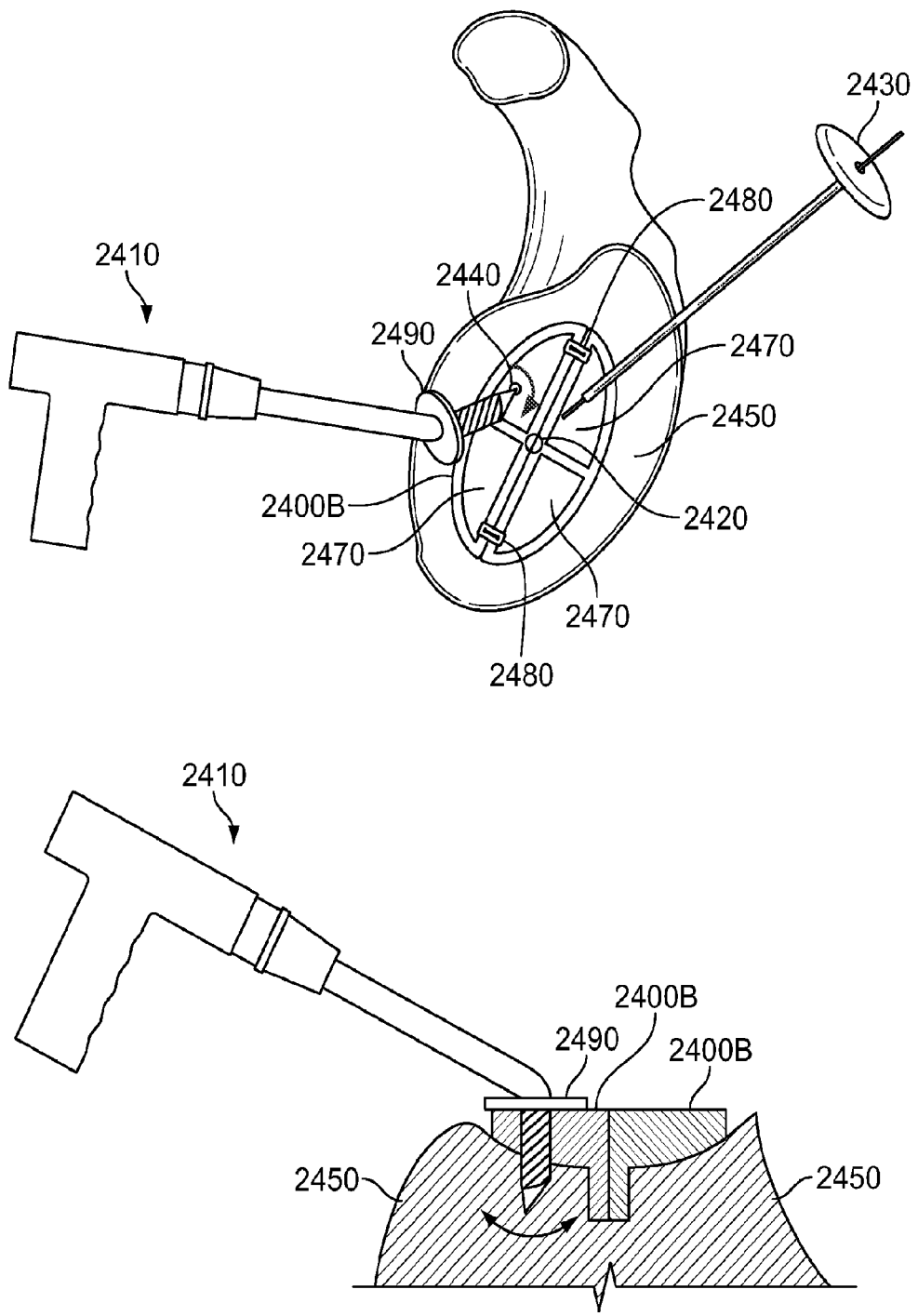
Figures 1, 24C:
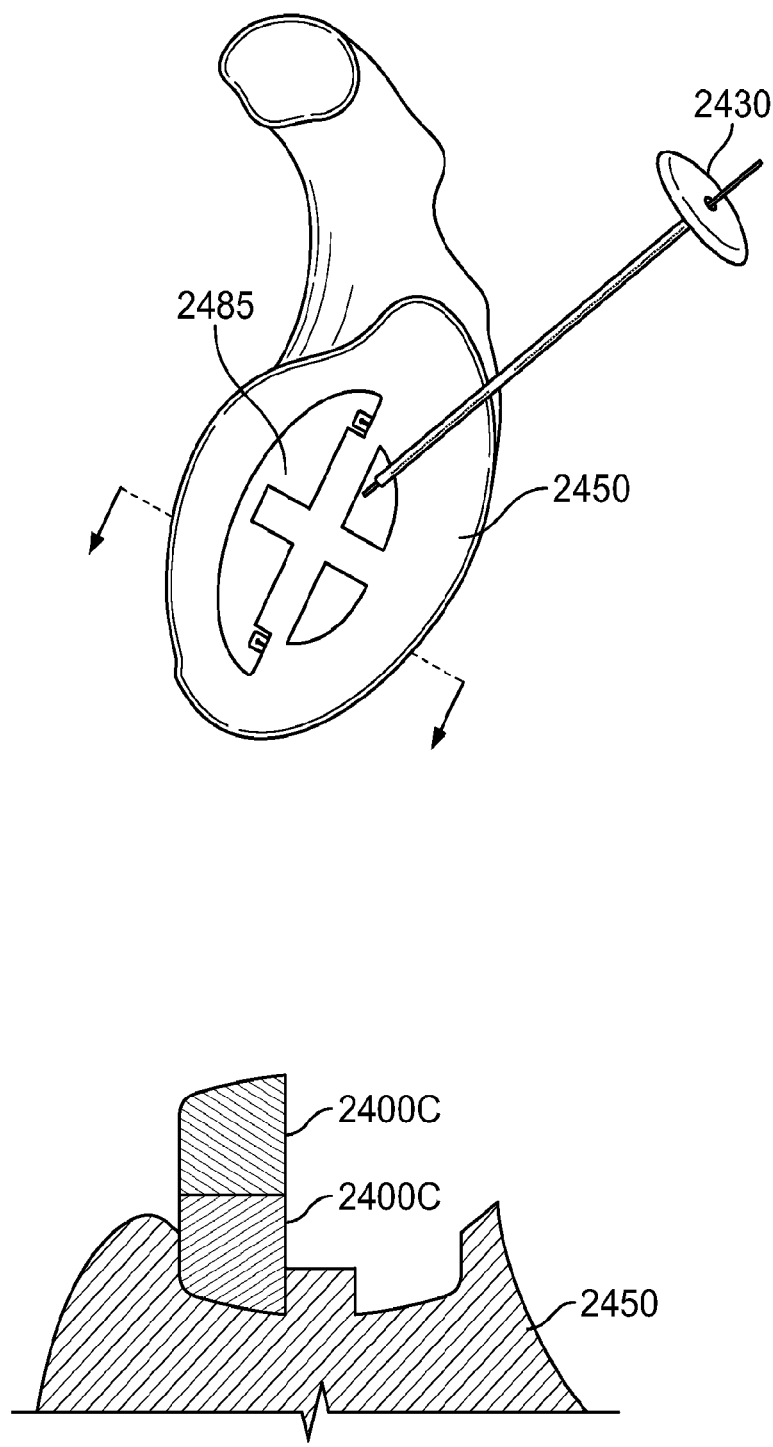
Figure 24C:
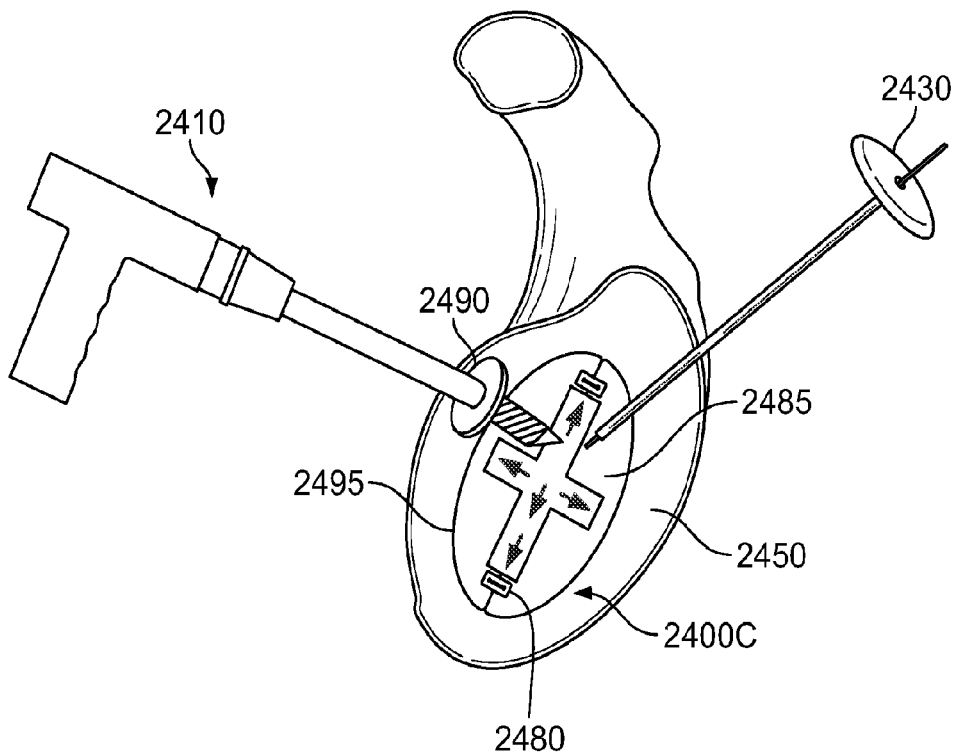
Figure 2:
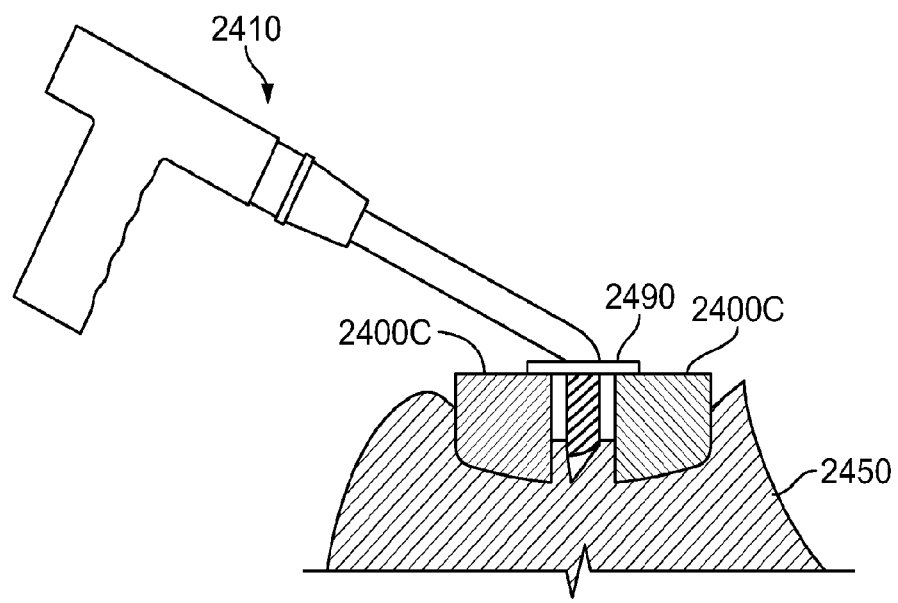

FIG. 24C-1 shows an unfolded opened t-shape template 2400C being introduced into a shoulder joint. Once the opened t-shape template 2400C engages the glenoid, as shown in FIG. 24C-2, the plates 2485 unfold along the hinges 2480 and leave open a t-shaped channel 2495 to be routered. The plates 2485 may have approximately the same size depth and engage the glenoid to secure the plates 2485. A router 2410 may then be used to drill the desired depth. A collar 2490 may be used in conjunction with the router 2410 so the collar engages the plates 2485 and limits the depth the router may travel. The collar may be located at any desired location on the router. The depth of the router may be approximately the same as the metal templates.

Figure 24D:
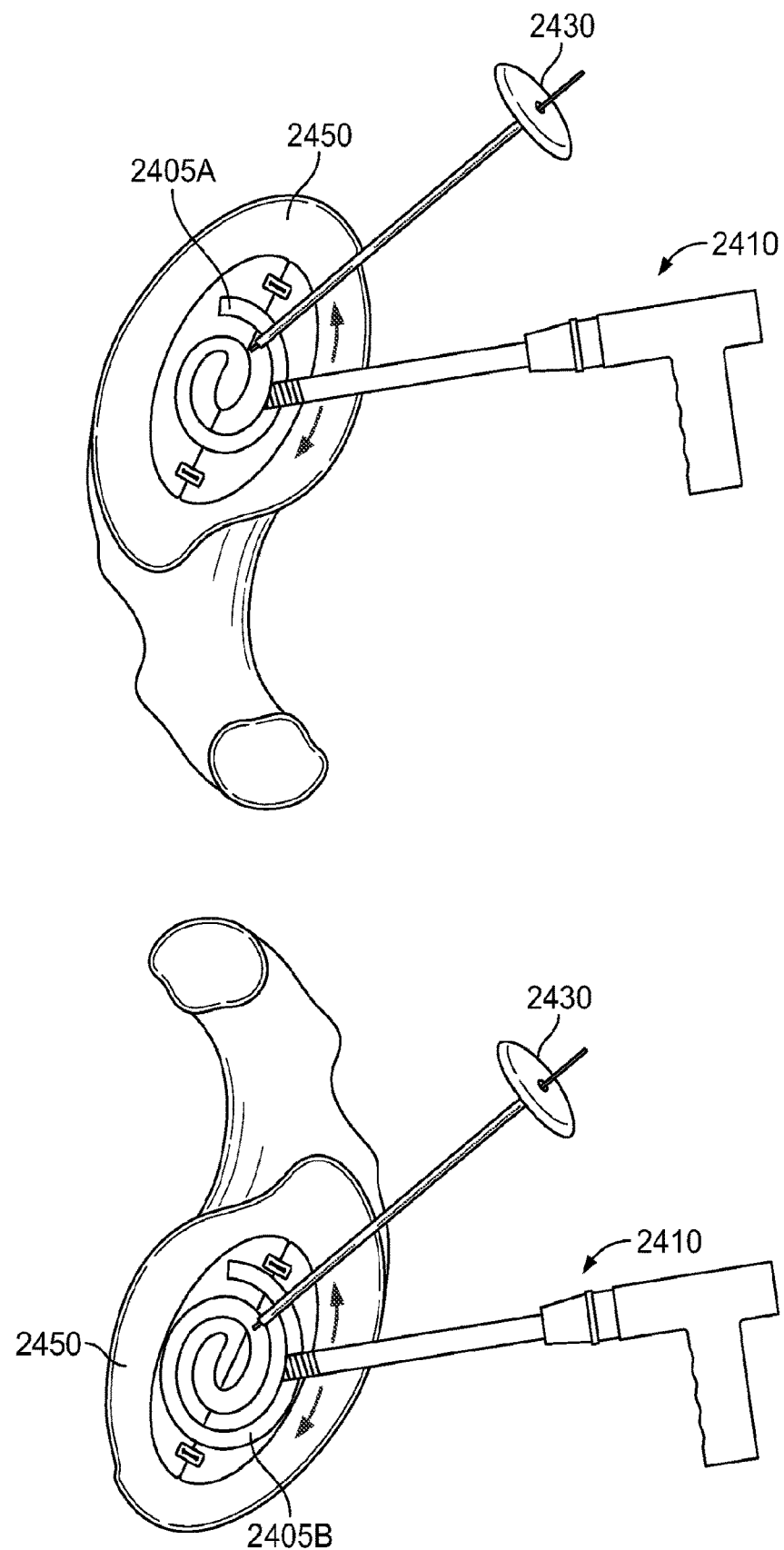
FIG. 24D is a schematic view of an embodiment of a template and a router/mill device wherein the template is milled in a spiral fashion.

Bone may be milled in spiral fashion as shown in FIG. 24D. In an embodiment, a first template may be spiraled in one direction, followed by a second template which would router out and is spiraled in the opposite direction to complete the desired shape. In another embodiment, two templates may be sequentially spiraled in a matching fashion to complete a desired shape. As shown in FIG. 24D, a first template is engaged with a shoulder joint and a first spiral 2405A eminates from the center, this cuts one channel into bone with a collared router. A second template is then placed into the joint with the first cut spiral to enable cutting of a second channel 2405B that represents what remains after the first cut.

EXAMPLES

A non-limiting example of an embodiment in a potential use:

The shoulder will first be approached arthroscopically with about one to two 1 cm incisions to view and assess the joint. Osteophytes (bone spurs) may be removed with standard arthroscopic equipment. Release of tight capsular structures may be achieved in the same manner.

Next, the bone of the humerus is to be prepared. Preparation options may vary depending upon conceptualized options for final implants for the humerus.

The portion of the glenoid component that is introduced into the bone of the scapula is to be made of a roughened surface that allows the bone to adhere over time obviating the need for cement and ending with a stronger and potentially permanent adherence of bone to implant.

The implant will then sit flush with the native remaining peripheral bone and restore the articulating surface of the joint to its native position which may further prevent loosening.

Traditional open glenoid preparation is difficult to achieve due to poor visualization and exposure to the glenoid surface. It requires preparation devices that approach the surface in a perpendicular fashion. Typical devices are referred to as reamers that act similar to a circular grater to scrap the bone to an even and bleeding surface.

Low profile, and angulated or articulated, router or mill type devices that will mill or router a trough via a template applied to bone may be used such that a glenoid implant may be introduced flush to the surface. The placement of a glenoid implant flush will allow the implant itself to be of a thickness that is less than existing implants, and is flush with the surface, to prevent a rocking horse effect and thus loosening of the implant.

Reference has been made in detail to exemplary embodiments of the present invention, examples of which are illustrated in the accompanying drawings. It is to be understood that other embodiments may be utilized and structural and functional changes may be made without departing from the respective scope of the invention. Moreover, features of the various embodiments may be combined or altered without departing from the scope of the invention. As such, the description has been presented by way of illustration only and should not limit in any way the various alternatives and modifications that may be made to the illustrated embodiments and still be within the spirit and scope of the invention.

While the invention has been described with reference to various exemplary embodiments, it will be appreciated that modifications may occur to those skilled in the art, and the present application is intended to cover such modifications and inventions as fall within the spirit of the invention.

What is claimed is:

1. A template for preparing a glenoid cavity for a glenoid implant, the template comprising:
   first and second plates, wherein the first plate is foldable on to the second plate for insertion into an incision in tissue and wherein the first plate is unfoldable relative to the second plate and wherein the first and second plates being unfolded are configured for engaging a glenoid cavity; and
   one or more channels formed through the first and second plates, wherein the channels are configured to receive a milling head of a router.

2. The template of claim 1, further comprising an alignment aperture formed through the first and second plates and sized and shaped to receive a pin for securing the first and second plates during a router procedure.

3. The template of claim 1, wherein the one or more channels comprise windows formed through the first and second plates.

4. The template of claim 1, wherein the one or more channels comprise a spiral shape when the plates are in the unfolded position.

5. The template of claim 1, wherein the one or more channels comprise a t-shape shape when the plates are in the unfolded position.

6. The template of claim 1, further comprising one or more hinges operatively attaching the first and second plates together, wherein the first and second plates are foldable and unfoldable about the one or more hinges.

7. A template for preparing a glenoid cavity for a glenoid implant, the template comprising:
first and second plates, wherein the first and second plates are positionable from a foldable state to an unfoldable state, wherein in the foldable state the first plate is positioned on top of the second plate and the first and second plates are insertable into an incision in tissue and wherein the first and second plates in the unfolded state are configured to engage a glenoid cavity; and
one or more channels formed through the first and second plates, wherein the channels are configured to receive a milling head of a router.

8. The template of claim 7, further comprising an alignment aperture formed through the first and second plates and sized to receive a pin for securing the first and second plates during a router procedure.

9. The template of claim 7, wherein the one or more channels comprise windows formed through the first and second plates.

10. The template of claim 7, further comprising one or more hinges operatively attaching the first and second plates together, wherein the first and second plates are foldable about the one or more hinges.

11. A template for preparing a glenoid cavity for a glenoid implant, the template comprising:
first and second plates;
one or more hinges operatively attaching the first and second plates together, wherein the first and second plates are swingable about the one or more hinges to a folded state for insertion into an incision in tissue where the first plate is positioned on top of or below the second plate and wherein the first and second plates are swingable about the one or more hinges to an unfolded state adapted for engaging a glenoid cavity; and
one or more channels formed through the first and second plates, wherein the channels are configured to receive a milling head of a router.

12. The template of claim 11, further comprising an alignment aperture formed through the first and second plates and sized to receive a pin for securing the first and second plates during a router procedure.

13. The template of claim 11, wherein the one or more channels comprise windows formed through the first and second plates.

* * * * *